(12) United States Patent
Druilhe et al.

(10) Patent No.: US 8,765,145 B2
(45) Date of Patent: Jul. 1, 2014

(54) **LSA-5 LIVER STAGE AND BLOOD STAGE ANTIGEN OF *PLASMODIUM FALCIPARUM*, IMMUNOGENIC COMPOSITION COMPRISING SAID ANTIGEN, AND VACCINES AGAINST MALARIA**

(75) Inventors: Pierre Druilhe, Paris (FR); Karima Brahimi-Zeghidour, Paris (FR)

(73) Assignee: Vac-4-All Pte. Ltd., Singapore (SG)

( * ) Notice: Subject to any disclaimer, the term of this patent is extended or adjusted under 35 U.S.C. 154(b) by 598 days.

(21) Appl. No.: 11/451,324

(22) Filed: Jun. 13, 2006

(65) Prior Publication Data

US 2010/0183590 A1    Jul. 22, 2010

Related U.S. Application Data

(63) Continuation of application No. PCT/EP2004/014848, filed on Dec. 15, 2004.

(30) Foreign Application Priority Data

Dec. 15, 2003  (EP) .................................... 03293158

(51) Int. Cl.
 *A61K 39/002*   (2006.01)
(52) U.S. Cl.
 USPC .................... 424/269.1; 424/272.1; 530/300; 530/350; 435/975
(58) Field of Classification Search
 None
 See application file for complete search history.

(56) References Cited

FOREIGN PATENT DOCUMENTS

WO   WO 86/00620       1/1986
WO   WO 02/38176 A2   5/2002

OTHER PUBLICATIONS

Greenspan et al (Nature Biotechnology 7: 936-937, 1999).*
Chothia et al (The EMBO Journal, 1986, 5/4:823-26).*
Mikayama et al. (Nov. 1993. Proc.Natl.Acad.Sci. USA, vol. 90 : 10056-10060).*
Rudinger et al. (Jun. 1976. Peptide Hormones. Biol.Council. pp. 5-7).*
Koenen, M. et al., "Human Antisera Detects a *Plasmodium falciparum* Genomic Clone Encoding a Nonapeptide Repeat," Nature, vol. 311, No. 5984, pp. 382-385 (Sep. 27, 1984).
Gardner, M. J. et al., "Genome Sequence of the Human Malaria Parasite *Plasmodium falciparum*," Nature, vol. 419, pp. 498-511 (2002).
Database EMBL, "Gene 11-1 Protein Precursor," Database Accession No. Q8I6U6, XP00272412, (Mar. 1, 2003).
Database EMBL, "*P. falciparum* Beta-Galactosidase Fusion Protein Gene," Database Accession No. M32153, XP002272411, (Nov. 22, 1990).
NCBI, "*Plasmodium falciparum* 11-1 Gene Part 1," Accession No. X07453 X 66268, XP002272413, 3 pages (Mar. 25, 1993).
Bojang, K. A. et al., "Efficacy of RTS,S/AS02 Malaria Vaccine Against *Plasmodium falciparum* Infection in Semi-Immune Adult Men in The Gambia: a Radomised Trial," The Lancet, vol. 358, pp. 1927-1934, (Dec. 8, 2001).
Perlaza, B. L. et al., "Immunogenicity and Protective Efficacy of *Plasmodium falciparum* Liver-Stage Ag-3 in *Aotus Lemurinus Griseimembra* Monkeys," Eur J. Immunol., vol. 33, pp. 1321-1327, (2003).
Ballou, W. R. et al., "Pre-Erythrocytic Malaria Vaccines to Prevent *Plasmodium falciparum* Malaria," Perlman P. Troye-Blomberg M (eds): Malaria Immunology, Chem Immunol. Basel, Karger, vol. 80, pp. 253-261, (2002).
Kurtis, J. D. et al., "Pre-Erythrocytic Immunity to *Plasmodium falciparum*: The Case for an LSA-1 Vaccine," Trends in Parasitology, vol. 17, No. 5, pp. 219-223, (May 2001).
Moorthy, V. et al., "Marlaria Vaccines," British Medical Bulletin, vol. 62, pp. 59-72, (2002).

* cited by examiner

*Primary Examiner* — Jennifer Graser

(74) *Attorney, Agent, or Firm* — Morgan, Lewis & Bockius LLP

(57) ABSTRACT

The present invention pertains to the protection against malaria. More particularly, the invention is based on the characterization of a novel liver and sporozoite-stage *P. falciparum* antigen, referred to as LSA-5. This antigen is highly antigenic and the prevalence of antibodies in subjects living in endemic areas is extremely high (ca. 90%). The invention concerns antigenic peptides, mixtures thereof, or polypeptides, mixotopes and conjugates comprising part of the sequence of LSA-5, as well as immunogenic compositions, vaccines and kits comprising these.

29 Claims, 16 Drawing Sheets

Figure 2:
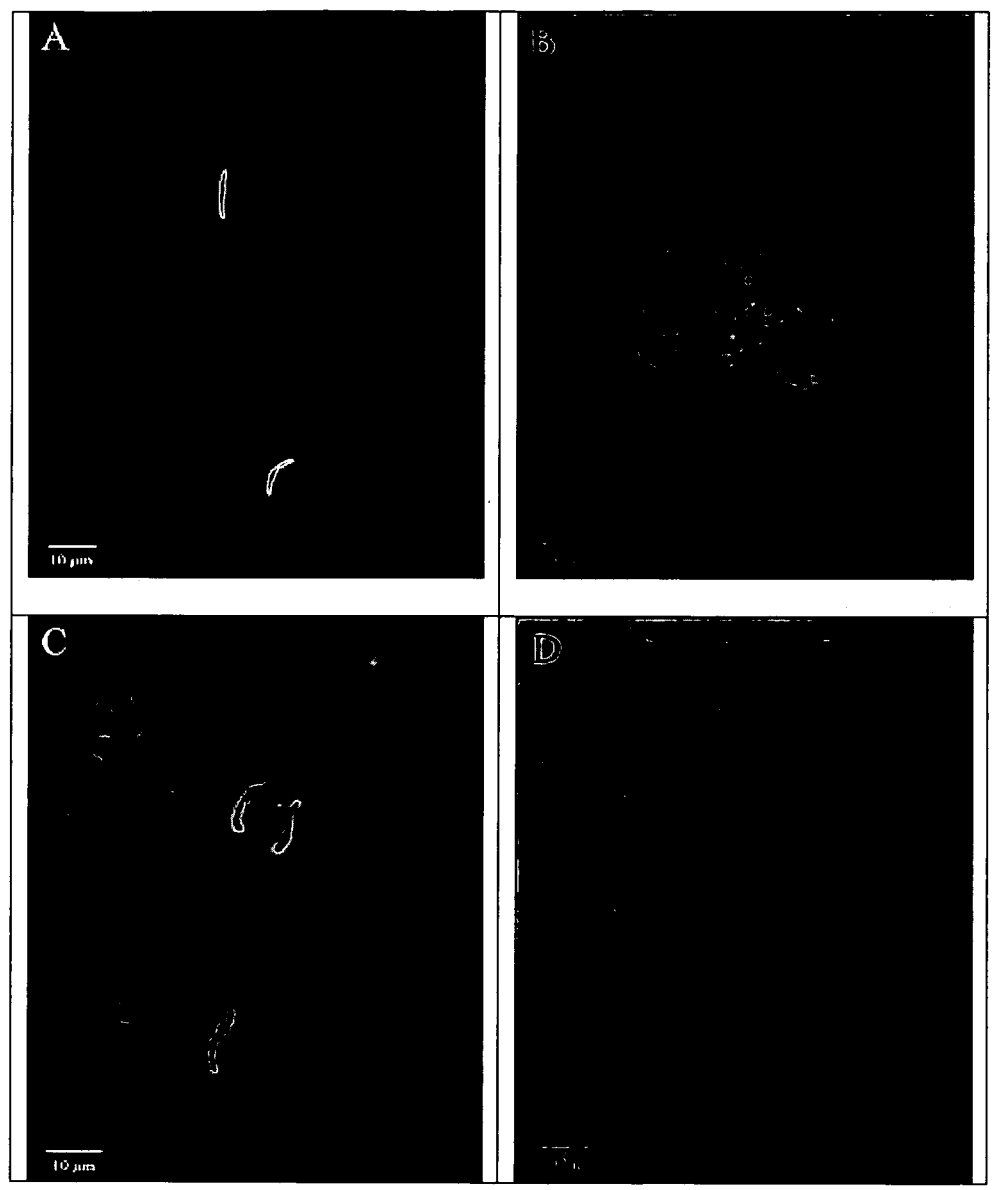

```
                        I P
              E E Q I E E V I
            Q E E I I E Q V V
            P E E L I E E V V
            P E E I I E E V I
            P E E I V E E V I
                    Y E E V I
            P E E L V E E V I
            A E K L V K E I V
            P E Q V R E E V T
            L E E I V E E M I
            P E E F V E E V A
            P E V E I E E I I
            P E E L I E E V I
            P E V L V E E A V
            P E E L I E K V I
            P
```

SEQUENCE OF PEPTIDES FROM 571

P9B            Y P E E L V E E V I P E E L V E E V I P K

571 CONSENSUS  E E V V E E L I E E V I P E E L V L(PALM)-CONH2

```
               E                 I   E       P   E
571 MIXOTOPE     E V V P E E L V E   V I   E V L V K(PALM)-CONH2
               K   I I           R   K     A   K I I
```

FIG. 1

FIGURE 5
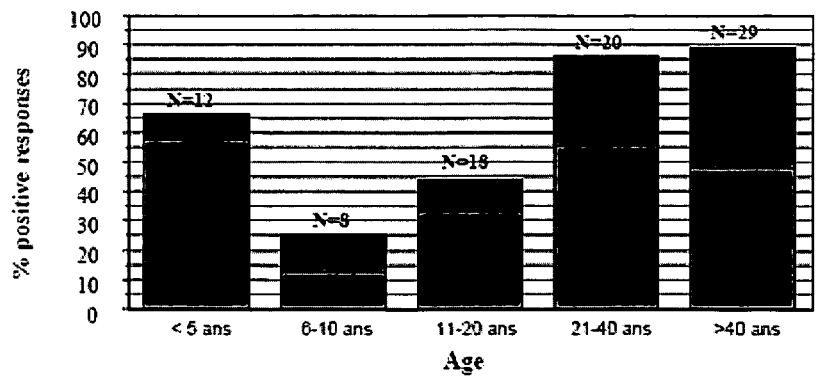
Figure 5. PREVALENCE % PODOR low transmission area (1-3 infected bites / year)
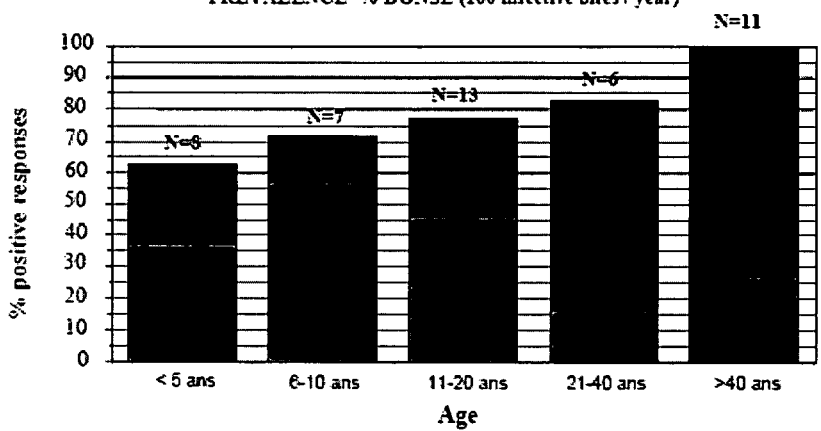
PREVALENCE % DONSE (100 infective bites / year)
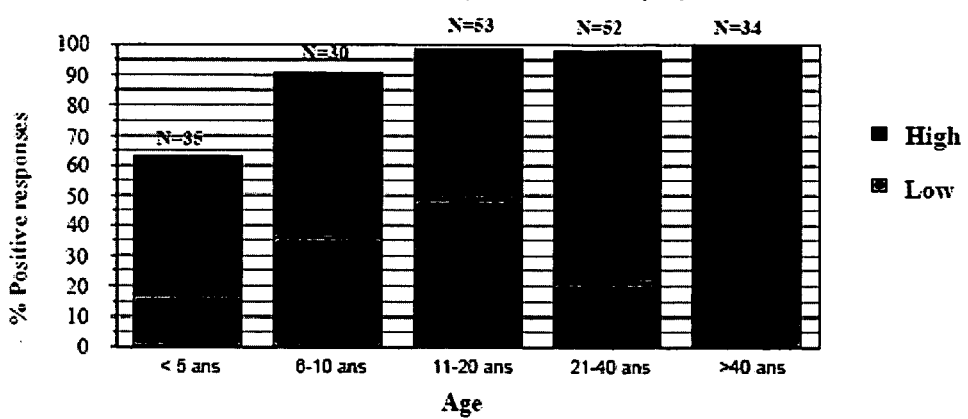
PREVALENCE % DIELMO (250 infective bites / year)

IFN-g Production (IU/ml)

PBMC in response to the recombinant protein

FIGURE 14

```
ATT CCA GAA GAA CAA ATT GAA GAG GTT ATA CAA GAA GAA
ATA ATT GAA CAA GTT GTA CCA GAA GAA TTA ATT GAA GAA
GTT GTA CCA GAA GAA ATA ATT GAA GAG GTT ATA CCA GAA
GAA ATA GTT GAA GAG GTA ATA TAT GAA GAG GTG ATA CCT
GAA GAA CTA GTA GAA GAA GTT ATA GCT GAG AAA CTG GTT
AAA GAG ATT GTA CCA GAA CAA GTT CGT GAA GAA GTA ACA
TTA GAG GAA ATC GTT GAG GAG ATG ATA CCC GAA GAA TTT
GTA GAA GAG GTT GCA CCA GAA GTT GAA ATC GAG GAA ATA
ATT CCT GAG GAA TTA ATA GAA GAA GTT ATA CCA GAG GTA
TTA GTT GAA GAG GCT GTA CCA GAA GAA CTA ATA GAA AAA
GTT ATA CC
```

LSA-5 LIVER STAGE AND BLOOD STAGE ANTIGEN OF *PLASMODIUM FALCIPARUM*, IMMUNOGENIC COMPOSITION COMPRISING SAID ANTIGEN, AND VACCINES AGAINST MALARIA

RELATED APPLICATIONS

This application is a continuation of International Patent Application PCT/EP04/14848, filed Dec. 15, 2004, which claims priority to European Patent Application EP 03293158, filed Dec. 15, 2003.

SEQUENCE LISTING SUBMISSION VIA EFS-WEB

A computer readable text file, entitled "045636-5179-SubstituteSequenceListing.txt" created on or about Oct. 3, 2013 with a file size of about 11 kb contains the sequence listing for this application and is hereby incorporated by reference in its entirety.

The present invention pertains to the protection against malaria. More particularly, the invention is based on the characterisation of a novel *P. falciparum* antigen hereafter referred to as LSA-5, expressed in sporozoïte-, liver- and blood-stage. This antigen is highly antigenic and the prevalence of antibodies in subjects living in endemic areas is extremely high (ca. 90%). The results described hereafter show that a) LSA-5 can be used to obtain a total sterilizing protection in a substantial number of immunized primates, against a challenge infection by a high dose of virulent sporozoite stage parasite from the species which is lethal for human beings and b) that antibodies induced by exposure to natural infection are very strongly associated with protection against malaria. Therefore, the present invention relates to new polypeptide molecules and to their use as active principle in antimalarial vaccine and in methods of diagnosis of the disease. Antibodies recognizing LSA-5, and their use in antimalarial therapy or diagnosis, is also contemplated.

The parasites responsible for malaria in man display different morphologies in the human host and express different antigens depending on their location in the body. The morphological and antigenic differences of these parasites during their life cycles in man enable different stages of development in the liver and in the blood to be defined: the sporozoïte, the infectious form injected by the vector mosquito, transforms rapidly into a schizont in the host's hepatocytes and thereafter infects the erythrocytes. The intrahepatic localization of *P. falciparum* manifests itself in the expression of a group of antigens specific to this stage of development and which are highly immunogenic under the natural conditions of exposure to the disease.

Complete sterile protection against malaria pre-erythrocytic stages can be obtained both in experimental hosts and in humans, by immunisation with irradiated sporozoites. It appears that what has long been considered an "anti-sporozoite immunity" is in fact related to the development of a liver-phase trophozoite and should be referred to as "liver-stage dependent immunity" (Druilhe et al, 1998).

The inventors have developed a methodology to identify *P. falciparum* liver stage antigens on the basis of screening a genomic expression library (of clone T9-96) with human stage restricted sera (from subjects exposed for to over 25 years to sporozoite inoculation, yet not developing blood forms due to continuous chloroquine prophylaxis). The clones were assigned to 29 genes, which all have the interesting characteristics to encode antigens recognised by exposed individuals (Druilhe et al, 1998, (Charlotte Gruner, Snounou et al. 2003). The initial screens for this family of clones included a) the pattern of expression in different stages of the life-cycle in various species and b) the study of conservation of the gene among *P. falciparum* wild isolates at sporozoite stage. Therefore, affinity-purified antibodies were prepared on the product of each clone, and used to study the reactivity with *P. falciparum*, *P. yoelii*, *P. berghei*, and to a certain extent, *P. vivax*, at a) sporozoite stage, b) liver stage and c) blood-stages. The degree of conservation was assessed by studying the expression of the antigen with the same antibody on the surface of a series of wild Thai isolates at sporozoite stage. Selected clones were further studied for their antigenicity, immunogenicity and protective efficacy. This has led to the characterisation of LSA-1 (liver stage antigen) described in WO 92/13884, SALSA (sporozoïte liver stage antigen) polypeptides described in EP A-0,407,230, STARP (Fidock, Bottius et al. 1994), and LSA-3 described in WO 96/41877.

As described in the experimental examples below, LSA-5 is most antigenic and immunogenic, well conserved among various isolates, and stands out, together with LSA-3, as one of the very few molecules able to induce a protective effect against a *P. falciparum* challenge. Moreover, the surrogates of protection are apparently similar for LSA-5, LSA-3 and irradiated sporozoites induced immunity, suggesting that all three may induce similar mechanisms of defence.

A first object of the present invention is hence an antigenic peptide or polypeptide comprising at least one motif (sequence) selected from the group consisting of SEQ ID No: 1 to 14 described in table 1 below, wherein said peptide or polypeptide is recognized by anti-LSA-5 specific antibodies. Antigenic peptides or polypeptides comprising at least one variant of one of the motifs of SEQ ID No: 1 to 14 are also part of the present invention, provided they are still recognized by anti-LSA-5 specific antibodies and provided said variant differs from one original motif in that one or several of its amino acid residue(s) is (are) replaced by the corresponding amino acid residue(s) of one or several of the other motifs.

Peptides consisting of sequence designated SEQ ID NO 3 or SEQ ID NO 4 are however excluded from the scope of the invention, in view of WO 86/00620. These peptides can however be included in the mixtures or mixotopes and can be used according to the applications of the invention.

|  | 1 | 2 | 3 | 4 | 5 | 6 | 7 | 8 | 9 |
|---|---|---|---|---|---|---|---|---|---|
| SEQ ID No.: 1 | E | E | Q | I | E | E | V | I | P |
| SEQ ID No.: 2 | E | E | I | I | E | Q | V | V | Q |
| SEQ ID No.: 3 | E | E | L | I | E | E | V | V | P |
| SEQ ID No.: 4 | E | E | I | I | E | E | V | I | P |
| SEQ ID No.: 5 | E | E | I | V | E | E | V | I | Y |
| SEQ ID No.: 6 |   |   |   |   | E | E | V | I | P |
| SEQ ID No.: 7 | E | E | L | V | E | E | V | I | A |
| SEQ ID No.: 8 | E | K | L | V | K | E | I | V | P |
| SEQ ID No.: 9 | E | Q | V | R | E | E | V | I | L |
| SEQ ID No.: 10 | E | E | I | V | E | E | V | A | P |
| SEQ ID No.: 11 | E | E | F | V | E | E | V | A | P |
| SEQ ID No.: 12 | E | V | E | I | E | E | I | I | P |
| SEQ ID No.: 13 | E | E | L | I | E | E | V | I | P |
| SEQ ID No.: 14 | E | E | L | I | E | K | V | I | P |

Table 1: Alignment of the amino acids sequence of the DG571 clone (SEQ ID No:16), showing the E, I, V-rich motifs that are present in LSA-5.

A particular group of sequences comprising the peptides (motifs) of SEQ No: 1 to 14 and their variants according to the present invention therefore comprises the peptide sequence of SEQ ID No:1, the peptide sequence of SEQ ID No:6, and the peptide sequences differing from SEQ ID No:1 and 6 as follows:
variants differing from SEQ ID No;1 in that:
the amino acid in second position is K, Q or V; and/or
the amino acid in third position is I, L, V, F or E; and/or
the amino acid in fourth position is V, or R; and/or
the amino acid in fifth position is K; and/or
the amino acid in sixth position is Q or K; and/or
the amino acid in seventh position is I; and/or
the amino acid in eighth position is P, V or A; and/or
the amino acid in ninth position is Q, A or L;
variants differing from SEQ ID No:6 in that:
the amino acid in first position is K; and/or
the amino acid in second position is Q or K; and/or
the amino acid in third position is I; and/or
the amino acid in fourth position is P, V or A; and/or
the amino acid in fifth position is Q, Y, A or L.

Such particular group of sequences can be included in a mixture of at least 2, especially at least 4 peptides selected among those of table 1 above.

An antigenic peptide or polypeptide comprising at least one variant of the motif of SEQ ID No: 1, as defined above, and which is recognized by anti-LSA-5 specific antibodies, is one particular embodiment of the present invention, and is especially used for the preparation of mixtures of peptides as defined above.

The peptides, polypeptides, or lipopetides according to the invention preferably comprise between 9 and 150 amino-acids, especially between 12 and 30 or 40 amino-acids in particular between 18 and 36 amino-acids.

The invention also relates to a mixture of peptides, resulting from the association of 2 or more, especially more than 3 peptides having an aminoacid sequence consisting of sequences selected from the group consisting of SEQ ID No: 1 to 14 described in Table 1.

In a particular embodiment, said mixture of peptides comprises or consists of at least 4, and has up to 14 different peptides selected from said group.

In another embodiment of said mixture of peptides, the peptides selected from the group disclosed above are associated with a consensus LSA-5 peptide described hereafter.

In a preferred embodiment, the mixture of peptides is prepared in such a way that it is immunogenic when the mixture is used for administration to a patient. Therefore, said mixture is advantageously representative of divergences observed between LSA-5 antigens in parasites in order to be used in a large group of patients.

In another embodiment of the invention, the mixture of peptides is constituted by a recombinant polypeptide resulting from the combination of 2 or more, especially more than 3 or 4 peptides, for example between 3 and 14 different peptides selected from the group consisting of SEQ ID No 1 to 14 described in Table 1, to which further peptides or polypeptides having a different sequence can be added, such as the consensus LSA-5 peptide disclosed hereafter.

The peptides or polypeptides of the invention can be obtained by chemical synthesis, or can be the product of recombinant expression.

The invention also pertains to a consensus LSA-5 peptide having the following sequence: EEVVEELIEEVIPEELVL (SEQ ID NO: 15), which can be linked to a lipidic molecule to form lipopeptides. An example of such a consensus lipopeptide is (EEWEELIEEVIPEELVL (Plm)-CONH2) (SEQ ID NO: 20), wherein Plm is a C-terminal palmitoylysylamide residue.

Another aspect of the invention is the LSA-5 antigen of SEQ ID No: 16 (sequence of DG571) itself, and any antigenic peptide or polypeptide, which comprises LSA-5 or a variant thereof derived from LSA-5 by addition, deletion, or conservative substitution of one or several amino acids, provided said peptide or polypeptide is recognized by anti-LSA-5 specific antibodies.

Such a variant is for example a polypeptide having more than 60%, especially more than 62% or more than 65% or even more than 70% identity or similarity (i.e. conservative substitutions) with the sequence of LSA-5 antigen corresponding to SEQ ID No: 16, said identity or similarity being determined when said sequences are aligned according to an optimal global alignment procedure and compared having recourse to the known methods, for example using the available versions of BLAST such as the version made available by the NCBI.

The peptides or polypeptides of the invention can be obtained either by biological synthesis in cells using an expression vector, or by chemical synthesis, for example following the solid phase peptide synthesis (SPPS) methodology described by R. B Merrifield in 1963 (*J. Am. Chem. Soc.* 85, 2149), or one of its subsequent derivatives such as Fmoc or t-Boc chemistries. The facultative addition of a lipidic molecule, to any of the peptides or polypeptides according to the invention can be performed by example using the technique described by Deprez et al. (Deprez, Gras-Masse et al. 1995).

A test to determine whether a peptide or polypeptide is "recognized by anti-LSA-5 specific antibodies" in the sense of the present invention is as follows: human anti-LSA-5 specific antibodies are obtained as described in the materials and methods below, and then a competition test between said peptide or polypeptide and the LSA-5 antigen of SEQ ID No: 16 is performed, by testing their ability to bind to the obtained human anti-LSA-5 specific antibodies. Alternatively, a binding test can be performed with anti-LSA5 antibodies induced in an animal immunized with the LSA-5 antigen of SEQ ID No: 16, or immunopurified, by performing direct ELISAs or Western Blots, or cellular tests involving lymphocytes from an animal immunized with the LSA-5 antigen, in the presence of the peptide or polypeptide to be tested. More detailed protocols to test whether a peptide or polypeptide is "recognized by anti-LSA-5 specific antibodies" are described in Example 9 below.

Other objects of the present invention are fusion proteins comprising an antigenic moiety which is a peptide or polypeptide recognized by anti-LSA-5 specific antibodies, as described above, and a second moiety, which is heterologous to the LSA-5 antigen. By "heterologous to LSA-5" is meant here that the sequence of this second moiety is not derived from LSA-5. In particular, any sequence having less than 40% or less than 30% of identity with the sequence of SEQ ID No: 16 will be considered as heterologous to LSA-5. Examples of such fusion proteins are described below, such as (βgal-DG571, Gluthatione-S-transferase-LSA5, and a fusion protein with a 6-Histidine-tail (SEQ ID NO: 23), wherein LSA-5 is in N-terminal position. Of course, any other fusion protein comprising a LSA-5 moiety is also part of the present invention, it being understood that "LSA-5 moiety" designates the LSA-5 antigen itself and any antigenic peptide or polypeptide derived from LSA-5 as described above, provided it is recognised by anti-LSA-5 specific antibodies.

The present invention also pertains to a LSA-5 mixotope. A "mixotope" is a convergent combinatorial library of peptides obtained by a unique synthesis, by adding several different amino acids simultaneously, instead of one, to the peptide fragment already obtained, thereby generating a controlled diversity of the obtained peptides (Gras-Masse, Ameisen et al. 1992). In particular, the LSA-5 mixotope according to the present invention comprises a variety of synthetic peptides having the sequence:

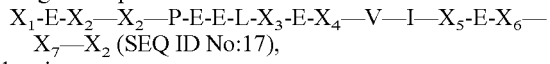

$X_1$-E-$X_2$—$X_2$—P-E-E-L-$X_3$-E-$X_4$—V—I—$X_5$-E-$X_6$—$X_7$—$X_2$ (SEQ ID No:17), wherein:

$X_1$=E, K, or none;
$X_2$=V or I;
$X_3$=I, V or R;
$X_4$=E or K;
$X_5$=P or A;
$X_6$=E, V or K;
$X_7$=L or I.

The mixotope of the invention is preferably a mix of at least 50, at least 100, is or at least 500 peptides of different sequences corresponding to SEQ ID No:17. When all the possible combinations are realised, the mixotope comprises up to 1152 different peptides.

A similar combinatorial library of peptides, or mixotope, can be obtained by preparing the mixotope according to sequences 1 to 14 of table 1, where each of the possible combinations is reproduced by the technique of the mixotope, including those that are not listed in table 1, but are possible, according to the aminoacid substitutions shown in table 1.

The invention also concerns a lipo-mixotope, which is a mixotope as defined above, in which at least part of the synthetic peptides is linked to a lipidic molecule. This lipidic molecule can be, for example, a palmitic acid, or any lipidic chain having 11 to 25 carbons.

In a particular aspect of the invention, the antigenic peptide, lipopeptide, polypeptide, lipo-polypeptide, peptides mixture, mixotope or lipo-mixotope is bound to a support. The invention therefore also relates to the conjugates obtained by covalent coupling of the peptides according to the invention to physiologically acceptable and non-toxic (natural or synthetic) carrier molecules that enable, in particular, the immunogenicity to be increased, via complementary reactive groups carried, respectively, by the carrier molecule and the peptide. Natural proteins such as tetanus toxoïd, ovalbumin, serum albumins, haemocyanins, tuberculin PPD (purified protein derivative), and the like, as well as viral particles such as Hepatitis B particles, may be mentioned as possible examples of macromolecular carrier molecules or supports which participate in the constitution of the conjugates according to the invention.

A preferred form of these conjugates is that which generates insoluble microparticles of 1 nanometer to 500 nanometers in diameter since such insoluble microparticles are preferentially taken up by Antigen Presenting Cells, particularly dendritic cells and channel the antigen into the antigen presenting pathways to lymphocytes. The practical value of particulate formulations obtained by linkage of the LSA-5 antigen with nitrocellulose particles or polystyren particles is described in example 5.

Biodegradable polymers, such as lipophosphoglycanes (LPG) or poly-L lactic acid, can advantageously used as supports in the conjugates according to the invention.

Synthetic macromolecular supports can also be used, like for example, polylysines or poly(DL-alanine)-poly(-Lysine) s.

Hydrocarbon or lipid supports, for example saturated or unsaturated fatty acids, and preferably $C_{16}$ or $C_{18}$ acids of the oleyl or palmitoleyl type, can also be coupled to the antigenic peptides or polypeptides according to the invention. Conjugates consisting of a polypeptide originating from LSA-5 covalently linked via a lysine bridge to saturated or unsaturated lipid residues hence also form part of the invention, more especially when the lipid residue is a palmitoyl or a palmityl or an oleyl.

Lastly and without implied limitation, the antigens or peptides according to the invention may be coupled to traditional supports or adsorbed on such supports, in particular nitrocellulose, latex or polystyrene microspheres or beads, or incorporated in Tyl particles.

To synthesize the conjugates according to the invention, use may be made of methods with are known per se, such as the one described by Frantz and Robertson in Infect. And Immunity, 33, 193-198 (1981), or the one described in Applied and Environmental Microbiology (October 1981), vol. 42, No. 4, 611-614 by P. E. Kauffman, using the peptide and the appropriate carrier molecule.

The invention also pertains to an immunogenic composition comprising as an immunogen a peptide, mixture of peptides, a polypeptide, especially a recombinant polypeptide, a lipopeptide, a lipo-polypeptide, a mixotope, a lipo-mixotope or a conjugate as defined above. For language simplification, the expression "peptide or polypeptide" will also designate and apply to, in what follows, lipopeptides, lipo-polypeptides, mixtures of peptides, polypeptides, including recombinant polypeptides, mixotopes and lipo-mixotopes, either bound to a support or not.

As shown in examples 5 and 6, immunisation with LSA-5 can induce a protection against *P. yoelii* challenge (in mice, cf. example 5) and *P. falciparum* challenge (in Aotus monkeys, cf. example 6). This demonstrates that LSA-5 is an excellent candidate for the preparation of an anti-malaria pre-erythrocytic sub-unit vaccine. The present invention therefore also pertains to the use of an immunogenic peptide or polypeptide according to the above definitions, for the preparation of a vaccine composition against malaria. A vaccine against malaria, comprising as an immunogen a peptide or polypeptide as defined above, is also part of the present invention.

As described in example 8, the association of LSA-5 with another antigen, in particular with LSA-3, leads to an increase in the immunogenicity of LSA-5. Therefore, immunogenic compositions and vaccines of the invention can further comprise a LSA-3 antigen as described by Daubersies et al. (2000), or a variant thereof recognized by LSA-3-specific antibodies. The definition of the variants of LSA-3 that can be used in association with LSA-5 corresponds to the polypeptide molecules defined in claim 1 of WO 96/41877. In these LSA-3/LSA-5 associations, the two antigens can be either covalently linked (for example, in a fusion protein), or not, as described in example 8.

Other antigens associations comprising LSA-5 are also contemplated according to the present invention. In particular, immunogenic compositions and vaccines of the invention can comprise, in addition to LSA-5, one or more other antigen(s) selected in the group of antigens comprising LSA-1, LSA-3, SALSA, STARP, TRAP, PfEXP1, CS, MSP-3, P126-CERP-SERA and GLURP.

In a particular embodiment of the invention, the immunogenic composition or the vaccine is formulated for subcutaneous, intradermal or intramuscular injection. When formulated for subcutaneous injection, the immunogenic composition or vaccine of the invention preferably comprises between 1 and 100 μg of antigenic peptide per injection dose, more preferably between 2 and 50 μg/dose.

Of course, usual adjuvants, such as Alum and/or Montanide, can be added to the immunogenic composition or vaccine of the invention. Other possible adjuvants that can be used in the immunogenic composition or vaccine of the invention are described in EP 1 201 250 A1, such as SB62, SB26, and SBAS2 (AsO2), this latter being particularly preferred.

As illustrated in Example 11, a preferred form of the vaccine, especially including combination with adjuvant, is one that induces antibodies capable of cooperating with blood monocytes, to achieve blood stage parasites killing, and particularly antibodies belonging to cytophilic classes, mainly IgG1 and IgG3 whose Fc fragment can bind to Fcγ receptors on blood leucocytes. Such antibodies can be monocyte-dependent, and their capacity to act can be assayed through an Antibody Dependent Cellular Inhibition (ADCI) mechanism designed to assess the capability of antibodies to inhibit the in vitro growth of *P. falciparum* in the presence of monocytes. The ADCI procedure has been disclosed in particular in Bouharoun-Tayoun H. et al, 1995, Bouharoun-Tayoun H. et al 1990, Theisen M. et al, 2000) It is believed that such antibodies would also mediate *P. falciparum* growth inhibition in vivo, which can be assayed for example in mice infected with *P. falciparum*.

As described in example 4 below, passive transfer of anti-LSA-5 antibodies can be useful at least to inhibit the parasite invasion into hepatocytes. Another important aspect of the present invention is hence a purified polyclonal serum or monoclonal antibody which recognizes the LSA-5 antigen of SEQ ID No:16, as well as its use in pharmaceutical compositions to protect by passive immunotherapy infected subjects and subjects presenting or likely to present the symptoms of the disease.

The polyclonal antibodies may be produced either by affinity-purification from sera of infected people, as described in the materials and methods below, or by any other method known by the skilled artisan, for example by immunizing mammals with the native or recombinant LSA-5 protein or with a peptide, mixture of peptides, lipopeptide, polypeptide, mixotope or lipo-mixotope according to the present invention, either alone or coupled to a carrier molecule, and possibly in the presence of an adjuvant. Protocols for obtaining such polyclonal sera are described in general handbooks such as "Handbook of Experimental Immunology", $5^{th}$ edition, D. M. Weir, L. A. Herzenberg, C. C. Blackwell and L. A. Herzenberg, eds. Blackwell Scientific Publications, Ltd., Edimburgh, 1997.

The monoclonal antibodies may be produced by the hybridoma technique in accordance with the standard procedures comprising:
the fusion of a myeloma cell with spleen cells of an animal previously immunized with one of the antigens according to the invention,
the culture of the hybridomas formed by the fusion of the aforementioned cells and,
the selection of those hybridomas capable of forming monoclonal antibodies recognizing the antigen used for the immunization of the animals.

The animals selected for the immunization may be for example mice.

Of these monoclonal antibodies the cytophilic monoclonal antibodies will be selected advantageously, i.e. those whose Fc fragment is capable of binding to the Fcγ receptor of the human monocytes. Such antibodies are especially of the IgG1 or IgG3 classes.

Another procedure for the production of antibodies may enable human monoclonal antibodies to be formed in vitro. To do this, B lymphocytes immortalised with, for example, the Epstein Barr virus are used. These lymphocytes may be taken from a person having been infected by *P. falciparum*. In this case, they make possible the production of monoclonal antibodies against several antigens without having recourse to in vitro stimulation by novel antigens.

Another possibility consists in fusing B lymphocytes immortalised as described above with human B lymphocytes stimulated in vitro beforehand with an antigen according to the invention against which it is desired to form monoclonal antibodies under culture conditions permitting the stimulation of the lymphocytes.

Reference will advantageously be made to the technique described by Desgranges C. et al. (1987, J. of Virological Methods, vol. 16, p:281-292) for the preparation of the human monoclonal antibodies of the invention.

Human recombinant antibodies can also be obtained by using the method described in WO 03/016354 (Nielsen Leif Kofoed et al).

It is also contemplated within the framework of the invention to produce human monoclonal antibodies by genetic recombination by carrying out an in vitro transfection of the gene coding for the variable part of the antibody into vectors infecting bacteria under conditions permitting the expression of a human immunoglobulin.

Finally, the present invention relates to any type of monoclonal antibody, chimeric or hybrid, or even any fragment of polyclonal or monoclonal antibody of the Fab or Fab'2 type, or even smaller fragments of the variable chains of the antibodies and exhibiting the same affinity characteristics for the epitopes of the LSA-5 antigenic polypeptide of SEQ ID No: 16.

Preferred monoclonal antibodies according to the invention are human antibodies of class IgG1 or IgG3, or antibodies obtained in animals and having cytophilic properties in man, directed against one or more of the antigens whose sequence was described above.

A medicament for passive immunotherapy or prophylaxy of malaria, comprising antibodies as described above, is also part of the present invention. Indeed, the LSA-5 antigen is present at the surface of sporozoites, and hence anti-LSA-5 antibodies can inhibit the penetration of sporozoites into hepatic cells.

This medicament can further comprise antibodies directed against (i.e., recognizing) at least one other antigen selected amongst LSA-1, LSA-3, LSA-5, SALSA, STARP, TRAP, PfEXP1, CS, MSP-3, P126-CERP-SERA and GLURP. These antibodies can be produced following the same protocols as those described above for anti-LSA-5 antibodies.

The inventors have also shown that anti-LSA-5 antibodies can also be useful in the preparation of a drug for prevention or for treatment blood stages of *Plasmodium*, especially *P. falciparum* infection.

Furthermore, the inventors have shown that anti-LSA-5 antibodies can be used for the preparation of a drug for the treatment of cerebral malaria patients.

In such a case anti-LSA-5 antibodies can be used in association or more generally in a treatment together with small molecule antimalarial drugs such as quinine, artesunate and/or mefloquine.

A method for lowering the parasitemia in a malarial patient, or for protecting against or treating *Plasmodium falciparum* in a subject presenting malarial symptoms, or likely to be infected by malaria, is also provided. Such a method consists in administering to said subject a medicament comprising anti-LSA-5 antibodies, as described above.

The invention also pertains to a method for the in vitro diagnosis of malaria in an individual likely to be infected by *P. falciparum*, which comprises the bringing of a biological sample from said individual into contact with an antigenic peptide a mixture of peptides, or a polypeptide or a mixotope of the invention, under conditions enabling the formation of antigen/antibody complexes between said antigenic peptides or polypeptide and the antibodies possibly present in the biological sample, and the in vitro detection of the antigen/antibody complexes possibly formed. Examples of biological samples that can be used to perform this method are red blood cells, white blood cells, serum or urine. Conditions enabling the formation of antigen/antibody complexes are known by the skilled artisan, and can be found for example in the "Handbook of Experimental Immunology", supra.

In the above method, in vitro diagnosis can be performed by an ELISA assay, for example using conditions described in the "Handbook of Experimental Immunology", supra.

The invention also relates to a procedure for monitoring the vaccination of the patient against infection with *P. falciparum*, starting from a biological sample such as blood, characterized in that it comprises:
- the placing of the biological sample likely to contain protective antibodies against *P. falciparum* in contact with at least one antigen according to the invention,
- the detection of the antigen-antibody reaction.

For carrying out these in vitro detection methods, the antigens according to the invention are advantageously labelled with the aid of a radioactive marker, an enzymatic or fluorescent label or even a physical type of marker.

In the diagnosis and monitoring methods described above, the biological sample can be further brought into contact with one or several antigenic peptides originating from other pre-erythrocytic antigens and/or from antigens of the sporozoite stage, for example with peptides originating from antigens selected amongst LSA-1, LSA-3, SALSA, STARP, TRAP, PfEXP1, CS, MSP-3, P126-CERP-SERA and GLURP.

The invention also relates to kits for the in vitro detection of the presence of antibodies directed against the antigens of the invention (for example, for the in vitro diagnosis of malaria, or for monitoring the vaccination against malaria), characterized in that they contain at least one peptide, especially mixture thereof, or polypeptide according to the invention, if necessary bound to a support. Advantageously, such a kit comprises:
- an antigenic composition comprising at least one antigen according to the invention, and optionally
- reagents necessary for carrying out the immunological reaction between the above-mentioned antigens and the antibodies possibly present in the biological sample, and/or
- reagents making possible the detection of the antigen-antibody complex produced by the immunological reaction. These reagents are for example labelled or capable of being recognized by a labelled reagent. These reagents can be for example subtrates and/or chromophores, when either the antigen or the antibody are labelled with a fluorophore.

Examples of reagents that can be included in the kits of the invention are described in the "Handbook of Experimental Immunology", supra.

Particular examples of kits according to the present invention are the following:
- an ELISA kit for detecting anti-LSA-5 antibodies, comprising a plate (or any solid support) which is pre-coated with LSA-5-derived antigens according to the invention. With this kit, the antibodies present in different liquids such as blood or serum are detected by contact with the antigen on the ELISA plate, followed by washing and visualization using a second antibody directed against the animal species in which said antibodies are sought (e.g., anti-human IgG secondary antibodies), said second antibody being labelled with an enzyme such as peroxydase or alkaline phosphatase, or a fluorescent molecule such as fluorescein, phycoerythrin etc., which enables the visualization of the fixing of the first antibody through a coloured, enzymatic, or fluorescent, or by any other means.
- An ELISA kit for detecting the LSA-5 antigen, comprising a plate (or any solid support) which is pre-coated with antibodies specific for said antigen. This kit enables to isolate the LSA-5 antigen from a biologic fluid such as blood, serum, urine, etc., in a capture test, and to visualize this capture through a second antibody specific for LSA-5 and labelled using any of the means described in the above paragraph.
- An immunocapture ELISA kit, enabling the detection of antibodies specific for the LSA-5 antigen, in which a plate (or any other solid support) is pre-coated with an antibody specific for immunoglobulins from the animal species in which the detection of anti-LSA5 antibodies is sought. Using such a kit, the sera from said animal species are incubated on the plate, and then the visualization of the antibodies that have been retained on the plate is performed with labelled LSA-5-derived peptides, according to what is described above.
- Immunochromatic kits, or dipsticks, are also contemplated. Such "fast kits" comprise one or several monoclonal antibodies capable of binding to the antigen, or antigens capable of binding to anti-LSA-5 antibodies.
- A kit comprising plastic beads for FACS (fluorescent-activated cell-sorter) analysis, wherein said beads are pre-coated either with an LSA-5 antigen, or by an anti-LSA-5 antibody, depending upon the element the detection of which is sought.
- Antibody- or antigen-microarrays, i.e., plastic or glass surfaces treated for fixing extremely low quantities of antibodies or antigens in conditions similar to those described above concerning the ELISA kits.

A kit according to the present invention also preferably comprises direction for its particular use.

Another method of the invention, for the in vitro diagnosis of malaria in an individual likely to be infected by *P. falciparum*, comprises the bringing of a biological sample from said individual into contact with anti-LSA-5 antibodies as described above, under conditions enabling the formation of antigen/antibody complexes between said antibodies and the antigens specific for *P. falciparum* possibly present in the biological sample, and the in vitro detection of the antigen/antibody complexes possibly formed. The biological samples that can be used in this method include blood, red blood cells, white blood cells, sera, and urine, for example.

A kit for the in vitro diagnosis of malaria, comprising anti-LSA-5 antibodies, is also part of the invention. Such a kit can further comprise reagents for enabling the formation of antigen/antibody complexes between said antibodies and LSA-5 antigens possibly present in a biological sample, and reagents enabling the in vitro detection of the antigen/antibody complexes possibly formed.

According to another aspect of the invention, the diagnosis of malaria can also be performed in vivo, by intra-dermic injection of an immunogenic composition comprising antigenic peptides or polypeptides as described above. Ready-to-use syringes or devices, comprising an appropriate amount of an immunogenic composition according to the invention, are also part of the invention.

Another aspect of the present invention is an isolated nucleotide sequence coding for an antigenic peptide or polypeptide as described above, as well as a recombinant nucleotide sequence comprising a promoter sequence and a sequence coding for such an antigenic peptide or polypeptide.

A particular sequence of the invention comprises the sequence of SEQ ID No:18, encoding the polypeptide of SEQ ID No.: 19 (i.e., a variant of LSA-5 antigen).

A recombinant cloning and/or, expression vector, comprising a nucleotide sequence as above-described, is also part of the invention. In this vector, the nucleotide sequence is preferably under the control of a promoter and regulatory elements homologous or heterologous vis-à-vis a host cell, for expression in the host cell.

The vectors of the invention can be used for the preparation of a medicament for genetic immunisation against *Plasmodium falciparum*. Accordingly, the invention also pertains to a DNA vaccine comprising a nucleotide sequence as described above. For example, the VR1020 vector (VICAL®), mentioned for example in (Kang, Calvo et al. 1998) and in (Valenzuela, Belkaid et al. 2001), can be used for obtaining constructs for direct DNA immunization.

A recombinant host cell, which is transformed by a vector according to the invention, is also part of the invention. This cell can be for example a bacterium, a yeast, an insect cell, or a mammalian cell.

The invention also concerns methods of immunisation of an individual likely to be infected by *P. falciparum*, by administering an immunogenic composition, a peptidic vaccine, or an expression vector or a DNA vaccine as described above. The skilled artisan is able to determine the best administration mode, depending on the type of composition used. For example, peptidic vaccine can be administered via subcutaneous injection, and a DNA vaccine can be administered by gene gun. For example, peptidic vaccine can be aministered via subcutaneous or intramuscular injection together with appropriate adjuvants, and a DNA vaccine can be administered by intra-dermic, subcutaneous or intra-muscular injection, by needle, by gene-gun or by powderject with or without enhancing sequences such as CPG.

Additional features of the invention will also become apparent in the following examples, illustrated with the figures, and show special features of the molecules of the invention.

LEGENDS TO THE FIGURES

FIG. 1: Peptidic sequence of DG571 (SEQ ID NO: 16) and derived peptides.

FIG. 2: Indirect immunofluorescence of *P. falciparum* and *P. yoelii* pre-eruthrocytic stages. (A) immunofluorescence of non fixed NF54 sporozoites and (B) on the liver schizonts of *P. falciparum* with human affinity purified mono-specific anti-LSA5.71. (C, D) IFAT on 17 XNL sporozoites and liver schizonts from *P. yoelii* labelled with the same antibodies.

Figure 3:
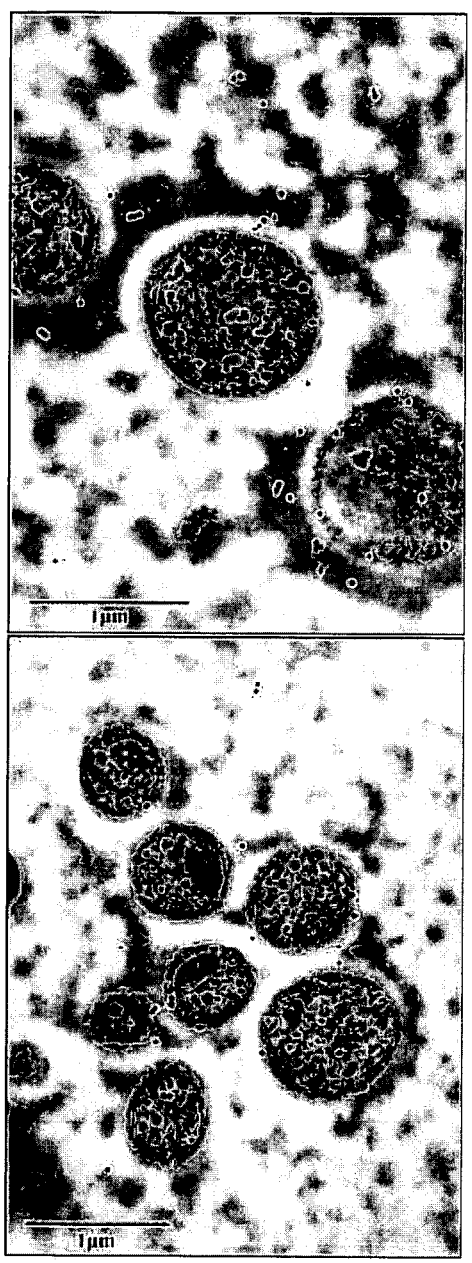

FIG. 3: Immunoelectronmicroscopy of *P. falciparum* NF54 sporozoites. Immunoelectro micrograph of *P. falciparum* sporozoites labeled with human affinity purified antibodies anti LSA-5.71 (β-galactosidase recombinant in λgt11), using as secondary gold-labelled antibody (15 nm).

Figure 4:
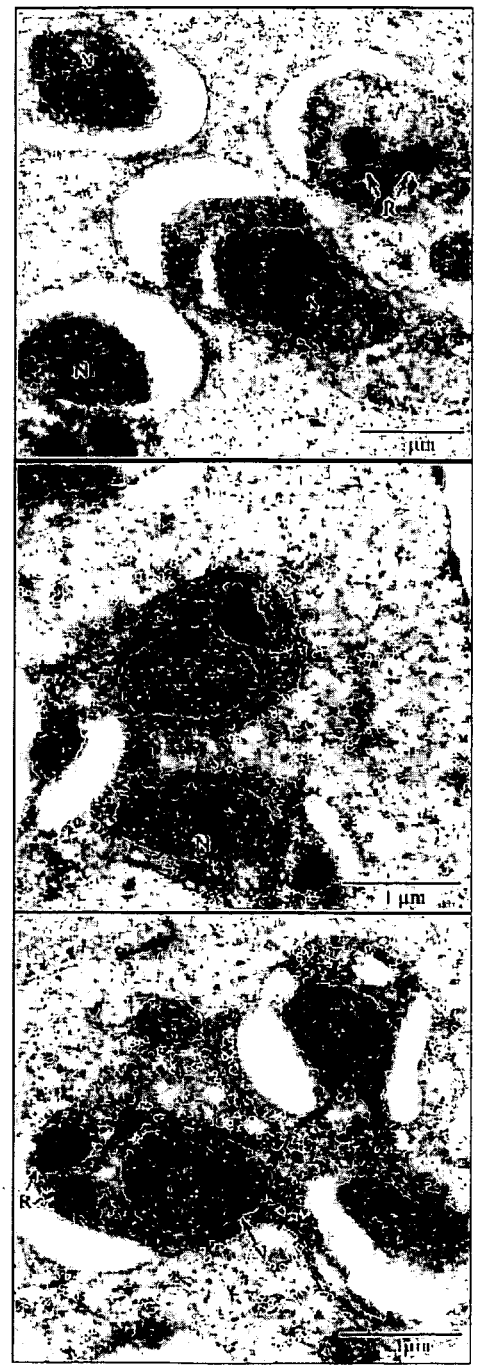

FIG. 4: Immunoelectron micrograph of mature (day 6) *P. falciparum* liver schizont labeled with human affinity purified antibodies anti-LSA-5.71 (β-gal recombinant) revealed by an anti-human gold labelled antibody (10 nm particle). LSA-5 is seen in the flocular material surrounding young emerging exoerythrocytic merozooites with clearly visible rhoptries (R) and nucleus (N). Control antibodies purified from β-gal were negative.

FIG. 5: PREVALENCE of anti LSA5 Abs in various endemic areas.

Figure 6:
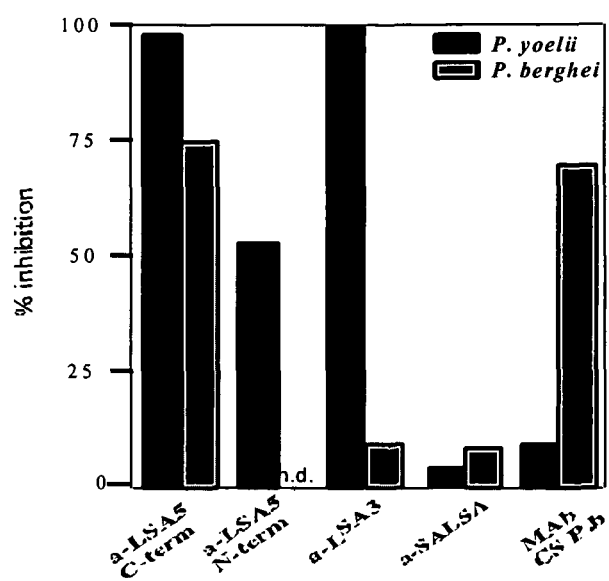

FIG. 6: Effect of anti-LSA-5 antibodies upon in vitro *P. yoelii* and *P. berghei* sporozoite invasion. Human antibodies from human hyperimmune sera were affinity purified on recombinant LSA-5-C-term or recombinant LSA-5-N-term and tested on in vitro invasion of primary cultures of mouse hepatocytes by *P. yoelii* or *P. berghei* sporozoites. Similarly, purified antibodies to LSA-3 or to SALSA proteins were tested as positive or negative controls for *P. yoelii*, respectively. One Monoclonal antibody to the *P. berghei* CSP was used as a positive control for *P. berghei*. The % inhibition was deduced from the number of hepatic schizonts obtained in assays without antibodies.

Figure 7:
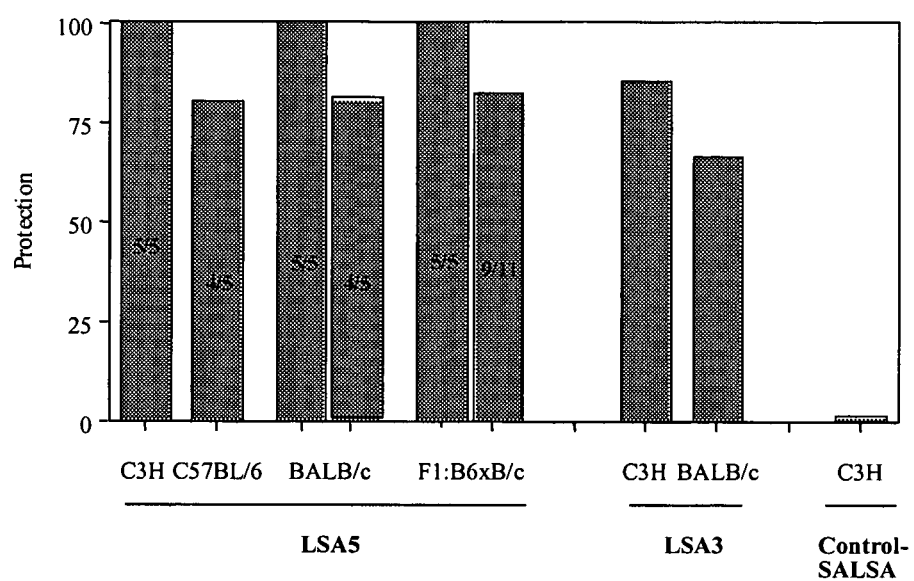

FIG. 7: Protection induced in mice by LSA5, as compared to LSA3, upon sporozoite challenge. Mice were immunised 3 times with 2 to 50 µg of recombinant LSA-5 or LSA-3 (DG729) or SALSA adsorbed onto microparticles. They were challenged by 1000 *P. yoelii* sporozoite (17XNL) injected IV. Blood stage parasitaemia was followed-up from day 4 to 14 after challenge.

Figure 8:
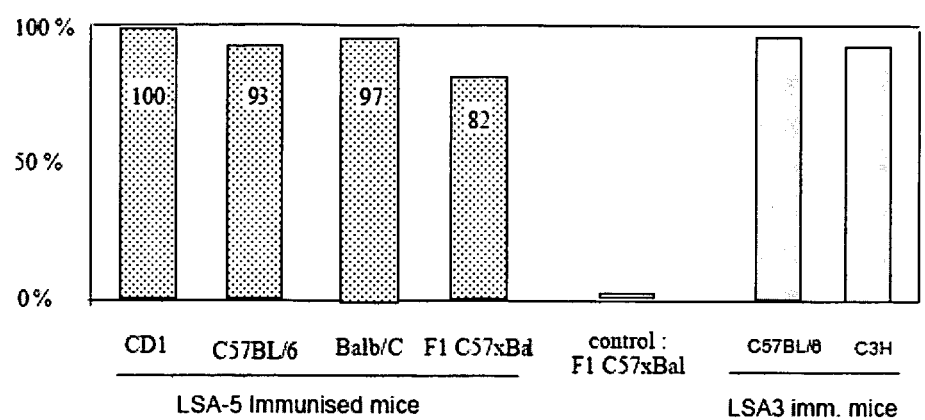

FIG. 8: Reduction in Liver Stages load in LSA-5 immunized mice challenged by 1 million *P. yoelii* sporozoites. After 42 h, the liver was taken from infected mice, the biopsies were fixed in Carnoy and embedded in paraffine. The number of liver schizonts was determined from 5 µg liver sections stained with the hematoxyline. Liver forms were enumerated in 100 sections per biopsy.

Figure 9:
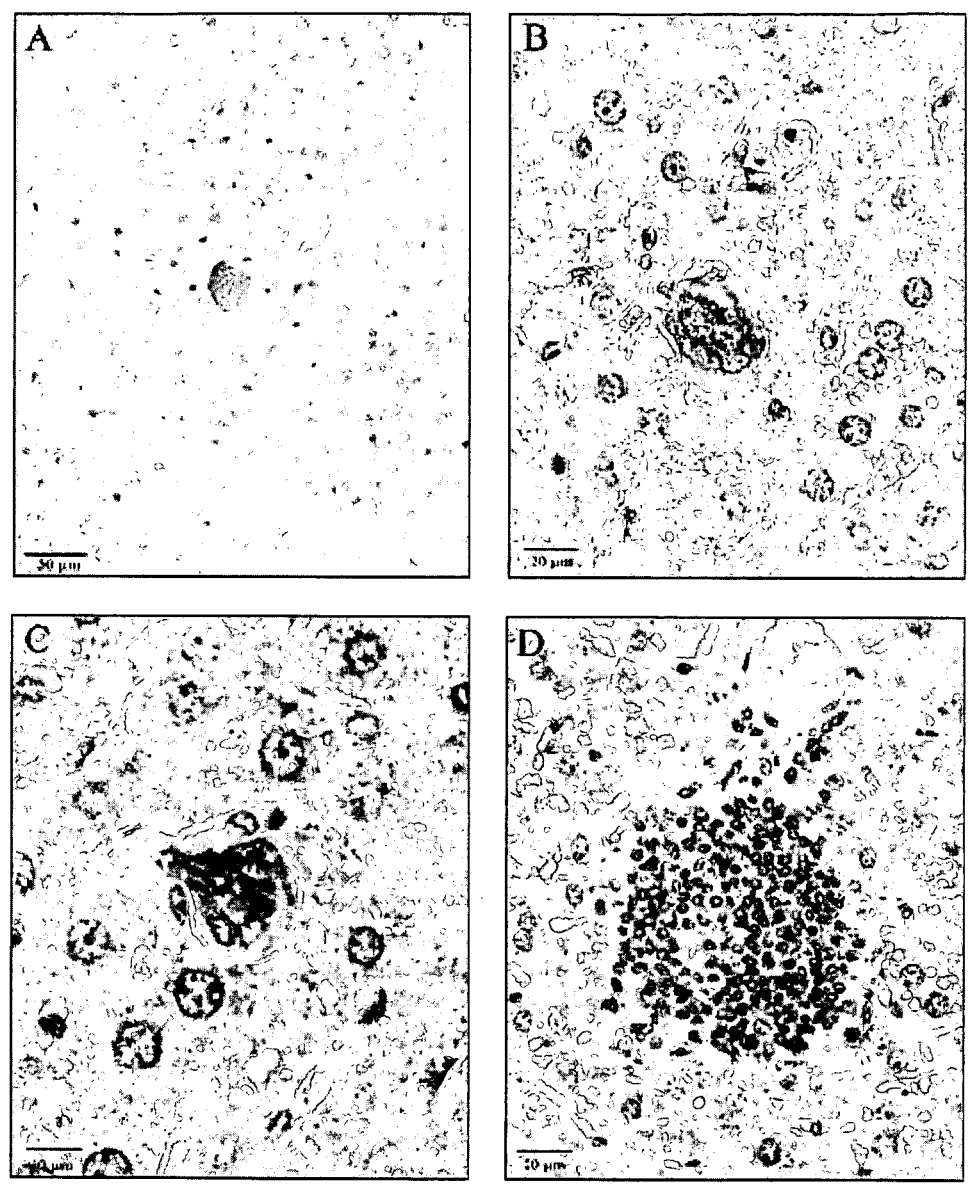

FIG. 9: In situ cellular events in the liver. LSA-5 immunised mice were challenged by intravenous inoculation of 1 million *P. yoelii* sporozoites. (A) healthy schizonts observed in control mouse (B,C) 2 liver schizonts infiltrated by mononuclear cells in the liver of C57BL6 immunised with β-gal-LSA-5.71 adsorbed on nitrocellulose particles. (D) cell granuloma where no residual schizonts can be seen in the same animal.

Figure 10:
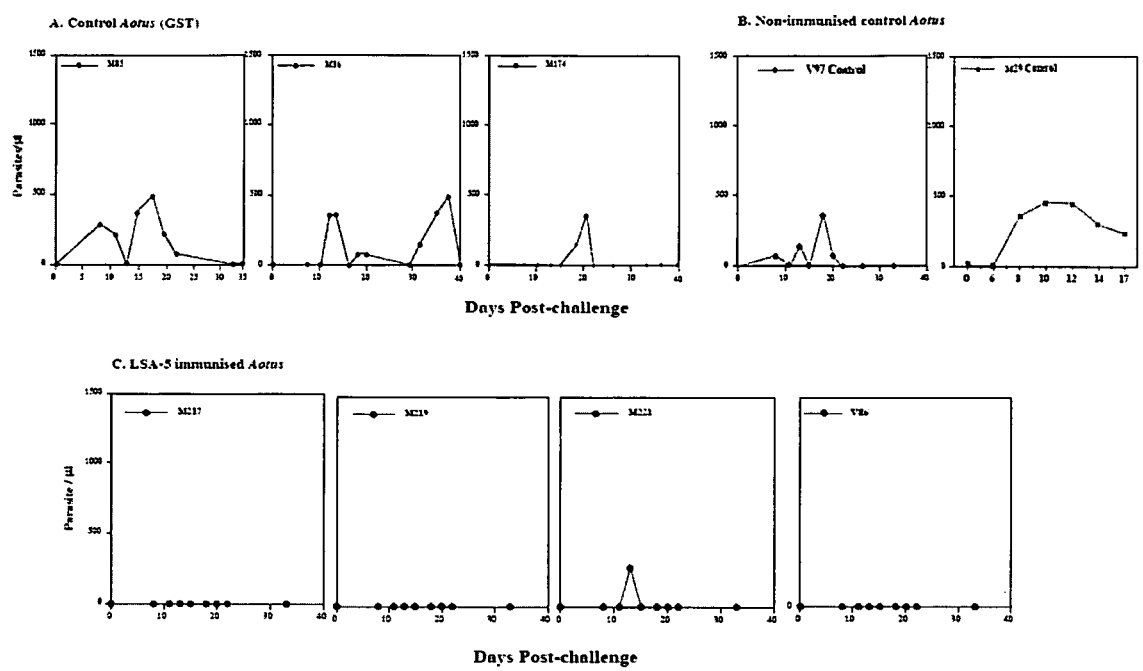

FIG. 10: Protection of Aotus immunised with Pf.LSA-5 after challenge with $10^6$ *P. falciparum* sporozoites.

Figure 11:
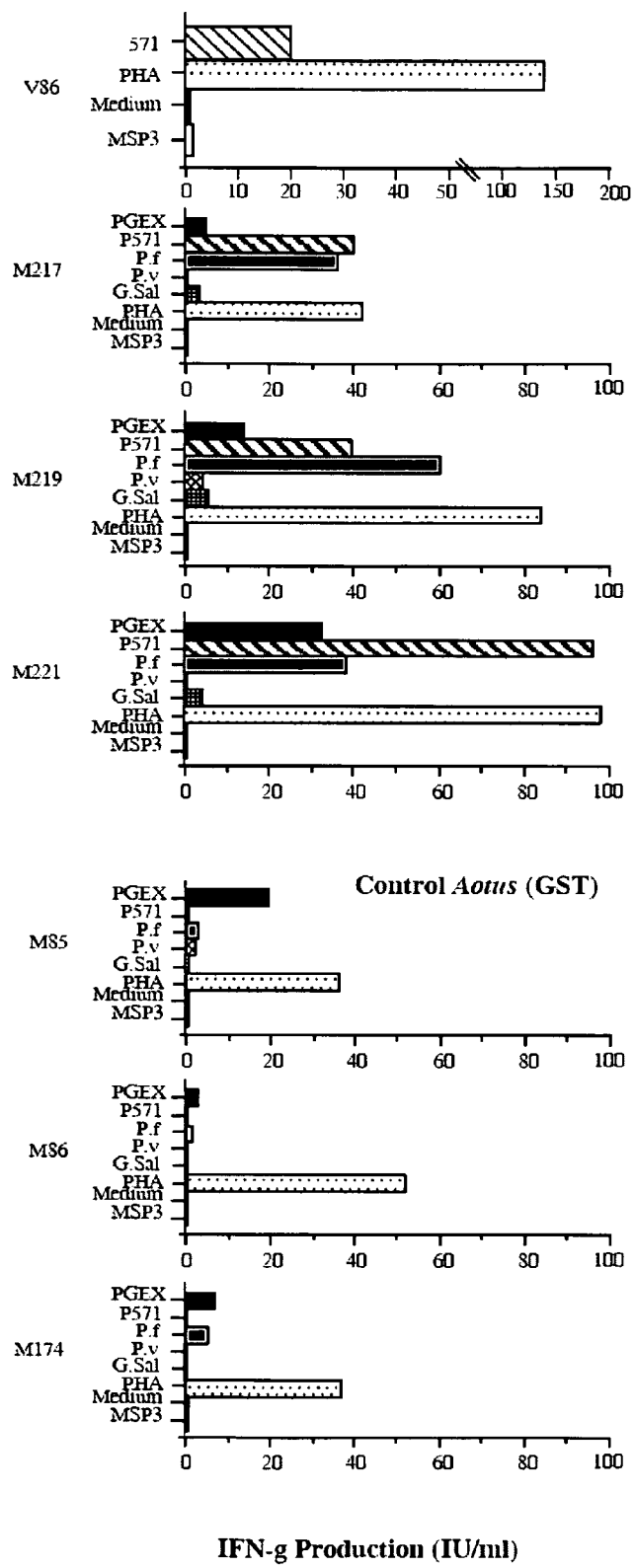

FIG. 11: IFN-γ Aotus/surnageants.

Figure 12:
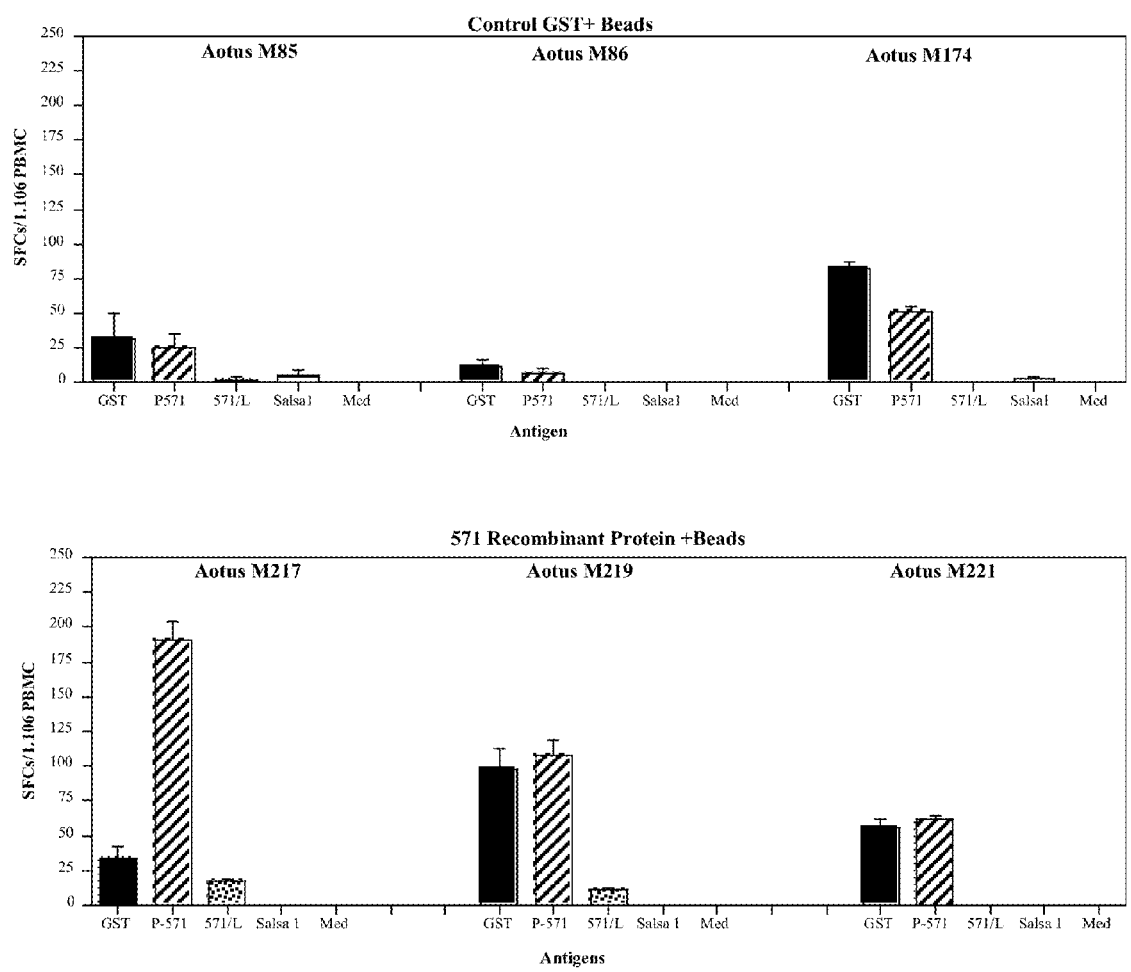

FIG. 12: ELISPOT Aotus.

Figure 13:
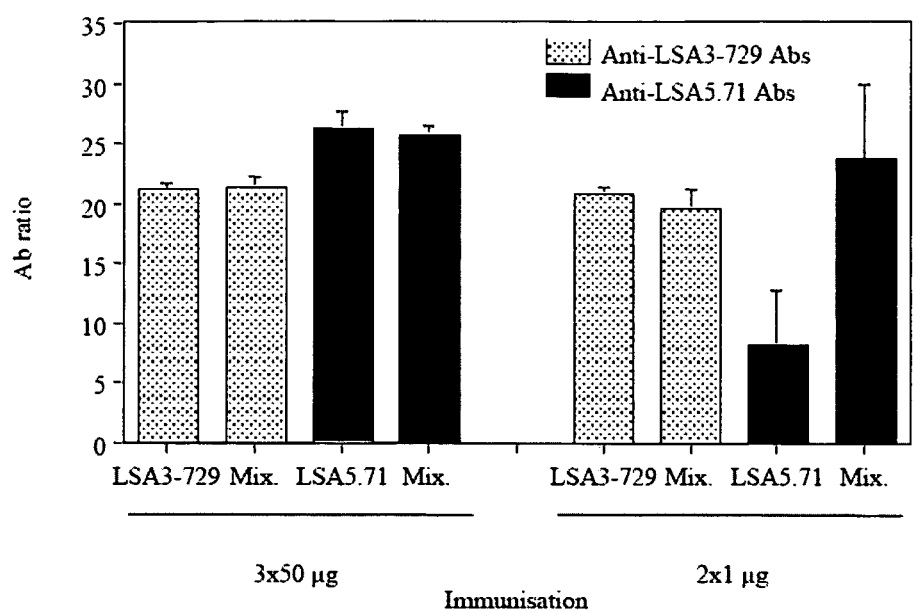

FIG. 13: Immunogenicity of LSA3 and LSA5 in mice immunised either with each or with both the proteins in a same mixture. C3H mice were immunised with 3×50 µg or 2×1 µg of recombinants LSA-3DG729 or LSA-5.71 or a mixture of LSA-3-DG729+LSA-5.71 in the adjuvant ASO2. Antibody responses were measured three weeks after the last immunisation by ELISA against each of the recombinants. Results are presented as means of Antibody ratio (+/−SD) from 5 mice per group compared to sera for unimmunised C3H mice.

FIG. 14: nucleotide sequence encoding a variant of the LSA-5 protein (SEQ ID NO:18).

Figure 15:
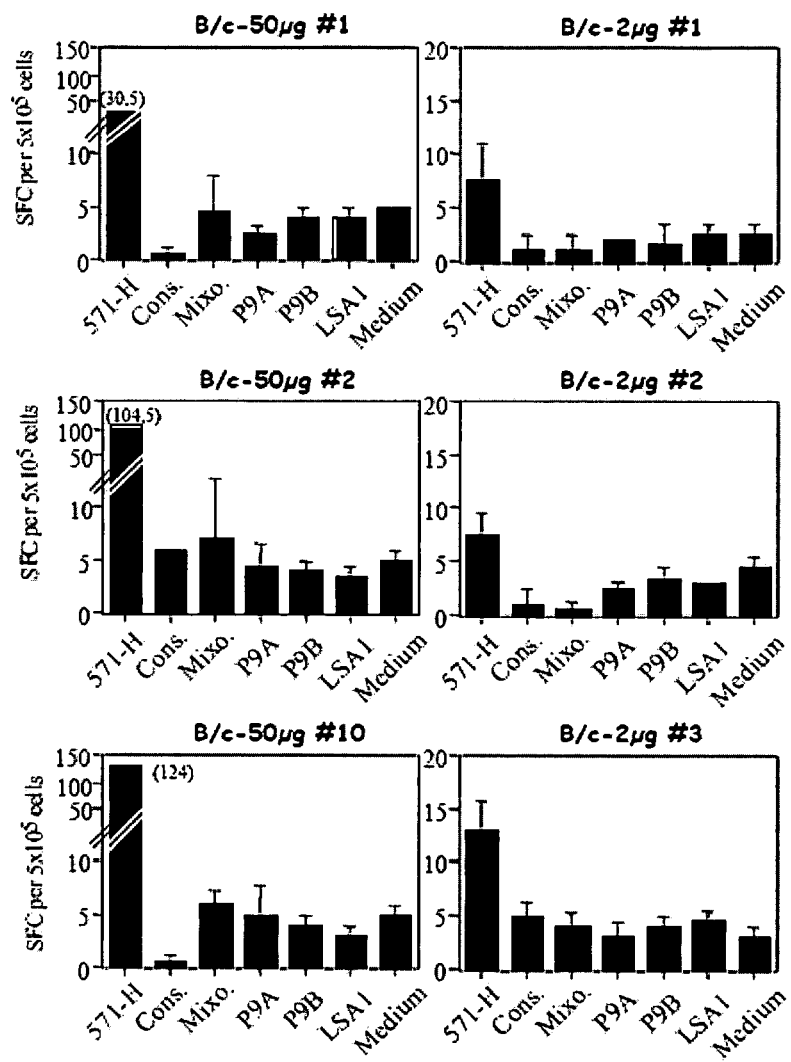

FIG. 15: BALB/c mice immunised with LSA-5 on microparticules: ELISPOT/IFN-g on spleen cells FIG. 16: C3H/Hej mice immunised with LSA-5 on microparticules: ELISPOT/IFN-g on spleen cells

EXAMPLES

The following examples have been performed using the materials and methods described hereafter:

Materials and Methods.

Sporozoites and Liver Forms

Sporozoites of *P. falciparum* were obtained either from infected *Anopheles gambiae* or *Anopheles dirus*, mosquitoes after membrane feeding on gametocytes from cultures of the NF54 as described by Ponnodurai (Ponnudurai, Lensen et al. 1989) or on gametocytes from 32 Thai patients, ie from wild Asian isolates (Galey, Druilhe et al. 1990).

Sporozoites of *P. yoelii* (17XNL strain, 17XNL clone 1.1 and 265BY) and *P. berghei* (Anka strain) were extracted from infected *A. stephensi*, 14 days and 18 days respectively after the mosquitoes were fed an infective mouse blood meal.

Sporozoites were prepared aseptically, fixed rapidly with 0.01% glutaraldehyde as described (Druilhe, Pradier et al. 1986) and stored at 4° C. before use for IFAT.

*P. falciparum* liver schizonts were obtained from liver biopsies of either a Sapajou monkey (Cebus appela), 5 days after infection with $10^6$ sporozoites of an African patient isolate 730XI (Druilhe, Puebla et al. 1984), or from a chimpanzee (Pantroglytes), day 6 post sporozoite infection with the NF54 strain (Meis, Ponnudurai et al. 1990).

*P. yoelii* liver schizonts were obtained from liver biopsies of C3H/HeJ mice 42 h after infection with $1\times10^6$ sporozoites of 17XNL clone 1.1.

Human Anti-LSA5 Specific Antibodies

Human antibodies were affinity-purified on the recombinant proteins βgal-DG 571 (LSA5) and βgal-DG 662 (PfEMP3) (Gruner, Brahimi et al. 2001) and βgal-DG 438 (Marchand and Druilhe 1990) by successive absorption of antibodies from seven human hyperimmune sera that had been depleted of Abs reactive with R-galactosidase (Brahimi, Perignon et al. 1993). Briefly, the recombinant proteins induced by and adsorbed on isopropylthiogalactoside-impregnated nitro-cellulose filters (BA 85, Schleicher & Schuell, Dassel, Germany), were incubated successively with each hyperimmune serum and washed extensively. Specifically binding Abs were recovered using 0.2 M glycine pH 2.5 and immediately neutralised by addition of 2 M Tris pH 11. Affinity-purified Abs were dialysed first against PBS pH 7.4, then against RPMI, in both cases over 24 h at 4° C. Samples were concentrated using a Centricon 30 membrane (Amicon, Millipore, USA) to a volume corresponding to a $\frac{1}{20}^{th}$ dilution of the original serum. Similar preparations were also made from GST and His6 recombinant LSA5.

Mouse anti-LSA5 sera have been obtained from mice immunised with βgal-DG571. The sera used in this study were collected 15 days after the third immunisation and stored frozen at −80° C. until use.

Indirect Fluorescent Antibody Test (IFAT)

The reactivity of human and animal antibodies with sporozoites and infected hepatocytes was assessed by incubating antibodies for thirty minutes at 37° C. with i) glutaraldehyde-fixed sporozoites, ii) 5 µm sections of LS infected liver tissue. The slides were then washed 3 times with PBS and incubated for a further 30 minutes with fluorescein isothiocyanate (FITC)-labeled goat anti-human IgG, A, M (Bio-Rad, France), or anti-mouse IgG, A, M (Cappel, Organon Teknika, Belgium), in all cases diluted 1/200 in PBS supplemented with 1/2000 Evans blue. Positivity by IFAT on liver schizonts was ascertained by phase contrast microscopy and subsequent Giemsa staining of the section (Druilhe, Puebla et al. 1984).

Immuno-Epidemiological Studies

Study Areas and Subjects.

The inventors relied on three endemic areas previously studied, thereby allowing for comparisons between antigens (Fidock, Gras-Masse et al. 1994; Trape, Rogier et al. 1994; Bottius, BenMohamed et al. 1996). The individuals covered all age-groups, ranging from 1 to 75 yr. The village of Podor is located in the northern part of Senegal, an extremely dry part of the Sahel. The transmission of malaria by mosquitoes is seasonal, and transmission was estimated to be on average one infective bite per person per year (range 1-5 infective bites/year). Donse is in the savannah part of Burkina Faso, 50 km north of Ouagadougou. Malaria transmission reaches 100 infective bite/individual/year (Druilhe, Pradier et al. 1986), which is high, although average by African standards.

Dielmo village is located in the Sine-Saloum region of Senegal. The transmission of malaria is intense and perennial with marked annual and seasonal fluctuations. The average of infective mosquito's bites is about 250/person/year.

Immunoblotting of Recombinant Proteins.

The recombinant proteins βgal-571 (LSA5) and βgal-64 (PfEMP3) were subjected to sodium dodecyl polyacrylamide gel electrophoresis on 7.5% acrylamide and electro-blotted onto nitrocellulose membrane. To study the prevalence of Ab to LSA5, and PfEMP3 recombinant molecules, 43 sera from Podor village were tested at 1/100 dilution and revealed by peroxidase-labeled second antibodies. As control, 9 sera from healthy individual were tested in parallel.

ELISA assay.

ELISAs were performed by coating microtiter plates with 10 µg/ml. solution in PBS of the LSA5-71 consensus peptide (EEVVEELIEEVIPEELVL (Plm)-$CONH_2$) (SEQ ID NO: 20) (FIG. 1). The plates were washed twice in PBS with 0.01% Tween 20, blocked for 1 h in PBS supplemented with 2.5% non-fat milk (Regilait) prior to addition of 50 µl of human sera at $\frac{1}{100}$ dilution in PBS 0.05% Tween 20 (PBST), 1.25% non-fat milk. The plates were then incubated at room temperature for one hour. After washing, the bound IgG were detected using peroxidase-conjugated goat anti-human IgG (H+L) (Byosis, Compiegne, france) added at a 1/4000 dilution in PBST 1.25% non-fat milk. Following incubation at room temperature for 1 h and a final wash, $H_2O_2$ and ortho-phenylenediamine (OPD, Sigma, St Louis) were added as substrates of peroxidase (0.03%, 1 mg/ml o-phenylene diamine, in 0, 1M citrate pH 5.5). After 30 minutes, absorbances were read at 450 nm on a Titertek Multiskan MCC/340 (Flow Laboratories, France). The results are expressed as the ratio of the mean O.D.s from test sera to the mean <O.D.+3SD from 10 healthy individuals studied in parallel in the same plates. Results are taken as positive for ratios >1.

Inhibition of Liver Stage Development Assay (ILSDA)

Human antibodies affinity purified upon the recombinant proteins LSA5-71 (DG571) and DG 88 (11.1) were tested for their inhibitory effect upon *P. falciparum* and *P. yoelii* invasion into primary cultures of human or mouse hepatocytes as previously described (Mellouk, Berbiguier et al. 1990). Human anti-DG671 (SALSA) antibodies were used as controls (Bottius, BenMohamed et al. 1996). Briefly, hepatocytes suspended in complete medium were seeded in eight-chambers Lab-Tek plastic slides (Nunc Inc., Napper Ville, Ill.) at a ratio of $10^5$ cells/chamber. After a 24 hr incubation at 37° C. in 5% $CO_2$ atmosphere, the medium was removed and Abs anti-DG571, anti-DG 88 or anti-SALSA Abs together $6\times10^4$ *P. falciparum*, *P. yoelii* or *P. berghei* sporozoites (NF54 strain, 17XNL clone 1.1 or ANKA strain respectively) suspended in culture medium were added to hepatocytes cultures. After 3 hr at 37° C., the medium containing antibodies and non-invaded sporozoites was discarded and replaced by fresh medium. Human hepatocytes were fixed after 96 hr of culture, and mouse hepatocytes after 44 hours, for 10 minutes in cold methanol. Developing *P. falciparum* or *P. yoelii* liver stages were identified by IFAT with either an anti-LSA1 (DG536) Ab or a monoclonal antibody (MAb) NYLS3 respectively, as described in (Charoenvit, Mellouk et al. 1995) by epifluorescence using an Olympus ultra violet (UV) microscope.

Parallel experiments were performed with *P. berghei* to evaluate inter-species inhibition. The MAb directed against the CS of *P. berghei* was used as control of inhibition of *P. berghei* sporozoite invasion and to detect *P. berghei* liver schizonts by IFAT staining as described in (Charoenvit, Mellouk et al. 1995). The total number of liver schizonts in each culture well was counted and used to calculate the mean number of the liver schizonts in duplicate culture wells. Results were expressed as the percentage of inhibition calculated as: (number of liver schizonts in control−number of liver schizonts in test/number of liver schizonts in control)×100.

In Vivo Passive Protection by Antibodies against Sporozoites Induced Infection

The in vivo effect of human affinity purified antibodies anti-LSA5 on the development of P. yoelii, was assessed as previously described (Brahimi, Badell et al. 2001). 0.2 ml of a solution of 100 µg/ml of either anti-LSA5-71, anti DG-729 (LSA3), and control human anti-DG671 (SALSA) specific antibodies, or RPMI, were added to 150 sporozoites of P. yoelii. Hence the final amount of Ab per mouse was 20 µg. The two components were mixed in a 1 ml syringe immediately before i.v. inoculation into the tail vein of BALB/c mice. Parasitaemiae were monitored from day 4 to day 21 by microscopic examination of Giemsa-stained thin smears of tail blood.

Immunogens

Most of the immunogenicity studies were performed using the initially identified clone LSA-5-71, which has been expressed in a large variety of vector systems for various types of antigen delivery, namely: as a β-galactosidase fused protein, expressed in the vector λGT11, as a Gluthatione-S-transferase fusion protein expressed in the vector PGEX, with the 6-Histidine-tail (SEQ ID NO: 23) expressed in the vector pTCRHis-6 (6×His taq disclosed as (SEQ ID NO: 23), and also for genetic immunisation using 2 different types of vectors, one which has been designed in the inventors' lab, the pNAK as well as the Vical patented vector VR1020. Part of the work was also performed using the 11.1 antigen clone DG88 expressed either in λGT11 or in His-tail vector.

Finally, immunisations were also performed using a lipomixotope peptide or convertope corresponding to a combinatorial library of synthetic peptides corresponding to each of the observed and potential substitutions in the sequence linked to a lipidic component, namely a palmitic-acid. For immunoassays, a Consensus peptide was also used, representing the sequence most frequently found among the repeats and as a comparison the P9B peptide derived from the 11.1 gene sequence (FIG. 1).

Immunisations and Challenges in Mice

1$^{st}$ Group:

C57BU6, BALB/c and F1: (C57BL/6xBALB/c) mice were immunised with 10 µg βgal-DG 571 adsorbed on microparticules of nitrocellulose at day 0 and received 3 subsequent injections of 5 µg of the recombinant protein at day 30, 100 and day 174.

The control groups were immunised with βgal-DG 671 (SALSA) as above.

2$^{nd}$ Group:

C3H/Hej, BALB/c mice were immunised with a higher dose of 50 µg GST-DG 571 adsorbed on 5.6×10$^4$ polystyrene beads (0.5 µm diameter) at day 0 and received two subsequent injection of 25 µg of the recombinant protein adsorbed on the same number of polystyrene beads at day 15 and day 36. C3H/Hej control mice were immunised with GST-DG671 (SALSA) as above.

P. yoelii Sporozoite Challenges

Low Dose.

1 month after the last immunisation, C57BL/6, BALB/c and F1: (C57BL/6xBALB/c) mice were challenged with 10000 live P. yoelii sporozoites (17XNL strain) and C3H/Hej mice were challenged with a lower dose (500 sporozoites from 17XNL clone 1.1) injected in the retro-orbital blood sinus, which is far more reliable than the tail-vein. Parasiteamia were determined on Giemsa stained blood smears from each mouse from day 5 to day 14. Protection was defined as either the absence of blood stages or a significant delay in their emergence as compared to controls, as described in (Sauzet, Perlaza et al. 2001), and as also applied today by A. Hill et at for clinical trials.

High Dose.

In this group, mice were challenged by 1 million live P. yoelii sporozoites i.v. The liver was removed 42 h-44 h post challenge. Each liver tissue was cut into 4 to 6 pieces and immediately fixed in Carnoy. The samples were embedded in paraffin sectioned at 5µ and stained with Hematoxylin-Eosine.

The number of hepatic schizonts was determined after observation of ≥100 sections from the different samples of infected liver tissue obtained from each animal. Only one every 10 sections was studied to avoid to count two times the same schizont.

Immunisations and Challenges of Aotus Monkeys

Immunisation Schedule.

Aotus lemurinus griseimembra from Primate Center (FU-CEP) of Immunology Institute-University of Valle-Cali, Colombia, were used. Only naive adults monkeys of no more than 800 g were included in the experiments. To avoid problems in the interpretation of the results about immunogenicity and protection, pregnant females or animals that have had previous malaria infections were excluded.

A total of 5 naive Aotus were immunised subcutaneously with 2 µg of GST DG 571-recombinant protein without adjuvant absorbed to polystyrene beads. This low antigen dose was chosen in view of comparative data obtained in mice both with LSA3 and LSA5, and of results in Aotus with LSA3 at the same dose (Perlaza, Zapata et al. 2003). Each animal received 3 doses of the immunogen at 21 days interval. Three Aotus were injected with GST alone and were used as antigen controls. Two additional naïve monkeys served as infectivity controls.

Sporozoite Challenge.

P. falciparum sporozoites were obtained from Anopheles albimanus mosquitoes fed on artificial feeders containing malaria infected blood from monkeys infected with P. falciparum Santa Lucia strain gametocytes. Sporozoites were collected in RPMI medium with normal monkey serum 14 days after mosquito feeding as described elsewhere (Hurtado, Salas et al. 1997). After mosquito salivary glands dissection, sporozoites were injected into the monkey femoral vein for challenges. Immunised and control groups received an infection with P. falciparum Santa Lucia sporozoites (Hurtado, Salas et al. 1997). Each Aotus was injected intravenously with a medium dose of 10$^5$ sporozoites. Two non-immunised Aotus (M29 and V97) received the same dose of sporozoites as controls of the batch infectivity. The parasitemia were followed-up during 40 days after challenge by thick smear, PCR and parasite LDH (pLDH) test. The parasite density expressed in parasites/pi was calculated as described elsewhere (Zapata, Perlaza et al. 2002). At the end of parasitemia follow-up, the animals were treated with a combination of Sulphadoxine-Pyrimethamine (Kinnamon and Rothe 1975; Landgraf, Kollaritsch et al. 1994).

IFN-γ Determinations.

PBMC from each monkey were isolated by gradient centrifugation on Ficoll Paque (Pharmacia Biotech) before immunisation and 15 days after the last injection for the determination of IFN-γ production. Upon in vitro stimulation with the antigens (10 µg/ml), IFN-γ production by PBMC was measured both by Elispot and in cell culture supernatants.

T-cell assays were performed using Aotus PBMC isolated on Ficoll Paque (Pharmacia Biotech) from the maximum ethically acceptable amount of blood from these small primates (less <1 Kg), i.e. 3 ml of blood taken by femoral venipuncture on day 0 (pre-immunisation) and 15 days after the third immunisation. The number of IFN-γ producing PBMC was evaluated using a commercial kit for human IFN-γ ELIspot (MABTECH, Stockholm, Sweden). Microtiter plate wells (Millipore, MAHA S45, Bedford, Mass., USA) were coated with 5 µg/ml of anti-human IFN-γ mAb (1-D1K MABTECH AB, Sweden) overnight at 4° C. After blocking with RPMI medium plus 10% foetal calf serum (FCS) for 2 h at room temperature, a suspension of $5 \times 10^5$ PBMC/well was mixed with either recombinant proteins or synthetic peptides at 20 µg/ml. Plates were incubated for 40 h at 37° C. in a 5% $CO_2$—95% air atmosphere. After washing with PBS-Tween-20 (PBS-T) 0.05%, a biotinylated anti-IFN-γ mAb (7-B6-1, MABTECH AB, Sweden) at 0.3 µg/ml was added and incubated overnight at 4° C. Streptavidine-alkaline phosphatase (Boehringer Mannheim) diluted 1/1000 was added and the reaction revealed with the substrate BCIP/NBT (5-bromo-2-chloro-3-indolyl Phosphatase/Nitroblue Tetrazolium) (Sigma, St Louis, Mo., U.S.A.) leading to the appearance of dark blue spots. The number of spots were determined using a stereomicroscope by two independent readers (x40). Results are expressed as the mean number of IFN-γ spot forming cells (SFCs) per $10^6$ PBMC. For quantitative reasons cells from one of the immunised Aotus could not be studied by this technique.

IFN-γ concentrations in PBMC supernatants collected on day 5 were determined by a two-site capture ELISA as describe elsewhere (Benmohamed, Thomas et al. 2000) using another combination of anti-human IFN-γ mAb identified as able to react with Aotus IFN-γ

Negative and positive controls (unstimulated cells and cells stimulated by PHA) were included in each assay. IFN-γ concentration (IU/ml) was calculated from a standard curve included in each plate and made from known amounts of recombinant human IFN-γ (Pharmingen International, 19751G). The specificity was determined by comparing the concentration in the test and control supernatants.

Combined Immunisation by LSA5 and LSA3

Groups of five C3H mice were immunised subcutaneously either a) three times at 1 month interval, with 50 µg of either the recombinant LSA3-DG729, or the recombinant LSA5.71, or a mixture of LSA3-DG729 +LSA5.71 or b) only two times at 1 month interval with only 1 µg of the same single or combined recombinants. All antigens were delivered s.c. with ASO2 adjuvant. Antibody responses were measured three weeks after the last immunisation by ELISA against each of the recombinants. Results are presented as means of Ab ratio (+/−SD) from 5 mice per group compared to sera from unimmunised C3H mice.

Example 1

Partial Characterisation of the LSA-5 Antigen

The initial clone identified, DG571, was found to be part of a group, or family, of 12 clones in the initial 119-pre-erythrocytic stage fragments, identified by screening with the serum of a priest exposed for 26 years to sporozoite challenges, while undergoing continuous daily chloroquine prophylaxis. The homologies between those clones were indicated not only by immunological cross-reactivity using affinity purified antibodies on the product of each of the 12 clones, but also by cross-hybridisation between those inserts. Sequencing of the fragments indicated that 7 had significant homology (>60%) with various regions of the gene encoding Pf11.1, whereas one belongs to GLURP and the 4 remaining contain repetitive sequences characteristic of the genome of *P. falciparum*. The sequence of the clone DG571, which corresponds to an insert of 399 base pairs, was found to be constituted of approximately 15 repeats of 9 amino-acids, rich in glutamic acid, isoleucine and valine (FIG. 1). For this reason, it has various degrees of homologies with other *P. falciparum* antigens rich in Glutamic acid, such as the R2 region of GLURP, the repeat region of LSA-3, the 11.1 antigen, the Pf332 antigen and the RESA.

Analysis of the released genome data did not lead to a clear-cut conclusion as to whether DG571 belongs to the megagene Pf11.1 or not. Indeed, whereas some clones had 100% homology with released sequence of 11.1, the degree of homology of DG571 at proteic level was only 55% (whereas it is 87% at nucleic acid level), ie. it was the most divergent of all (see Table 2). Moreover, the sequence of the Pf11.1 locus located on chromosome 10 is not entirely completed and the annotation is difficult in very large regions made only of repeats. Finally, the DG571 repeats appear to have unique immunological properties, since it was possible to induce protection by DG571 (see below), whereas protection was not induced by immunisation with the 11.1 type of repeats. Therefore, even if it belongs to 11.1, it is a rather unique sequence within, undescribed as yet.

TABLE 2

Antibody reactivity on sporozoites and liver stage.

| Antibodies | NF 54 | Wild isolates at sporozoite stage | | | | | | | | | | | LS | | | |
| | | XII | XIII | XIV | XV | XVI | XVII | XVIII | XIX | XX | XXI | XXII | Wild isol. Cebus | 3D7 chimp | *P. yoelii* spz | *P. berghei* spz |
|---|---|---|---|---|---|---|---|---|---|---|---|---|---|---|---|---|
| Anti LSA-5 Abs. | | | | | | | | | | | | | | | | |
| Hu-aff. Purified Abs. | +++ | +++ | +++ | +++ | +++ | +++ | +++ | +++ | +++ | +++ | +++ | +++ | +++ | +++ | +++ | ++ |
| Abs. raised in mice | +++ | NT | NT | NT | NT | +++ | +++ | +++ | +++ | +++ | +++ | +++ | NT | +++ | +++ | ++ |
| Control antibodie | | | | | | | | | | | | | | | | |
| Anti DG662 (PfEMP3) | + | NT | NT | NT | NT | 0 | ++ | ++ | 0 | 0 | + | ++ | | + | + | 0 |
| Anti DG438 | + | NT | NT | NT | NT | 0 | ++ | + | 0 | 0 | 0 | 0 | | + | 0 | 0 |

IFAT was performed with human anti-betaGal-DG571 (LSA-5) immunopurified mice on *P. faciparum* sporozoites from 11 Thai isolates and NF54 strain;

i) *P. falciparum* liver stages obtained from *Cebus apella* (5 day) and from chimpanzee (6 day) after sporozoites infection;

ii) *P. yoelii* (17XNL) and *P. berghei* (ANKA) sporozoites isolated from salivary glands of anopheles stephensi? Human anti betaGal-DG 662 (PfMP3) and anti-Beta-Gal-DG 438 immunopurified antibodies were used as control.

For the mice sera, the reactivity >=100 was considered positive. Affinity-purified antibodies were used undiluted: therefore, results are expressed as negative or positive.

Example 2

LSA-5 is Consistently Expressed on the Surface of Sporozoites from 32 Patient Isolates and in the Liver-Stages Human antibodies affinity-purified on LSA5-71 were found to be strongly reactive by IFAT (Immunofluorescent Antibody Test) with the surface of sporozoites from NF54, showing an evenly distributed labelling over the entire sporozoite surface. This reactivity was also detected on 12/12 thai isolates (Table 2). The pattern and the intensity of the fluorescence was the same for all sporozoites of each strain and isolates and was comparable to the reactivity obtained with the human anti-DG705 (clone corresponding to the CS gene) tested on the same samples (FIG. 2-A). In order to further evaluate the antigenic conservation of LSA5 amongst different *P. falciparum* isolates, IFA was performed using sporozoites from an additional 20 thai isolates and yielded the same consistent pattern of reactivity on each of them (not shown).

Human-specific anti-LSA5 antibodies were further tested by IFAT (indirect fluorescent antibody test) upon sporozoites from the two rodent malaria species *P. yoelii* and *P. berghei*. Similar pattern, with an even distribution over the entire surface of sporozoites was obtained with the two species although the reactivity was stronger with *P. yoelii* (FIG. 2-C). No IFAT labelling of *P. yoelii* or *P. berghei* sporozoites was obtained using human antibodies affinity-purified on the control recombinant protein DG 438, or using DG 662 (PfEMP3) on *P. berghei*. Antibodies induced in LSA5-immunised mice also strongly reacted with *P. falciparum* sporozoites from all the strains investigated (NF54 and 7 thai solates). The cross-reactivity on *P. yoelii* sporozoites (17XNL) obtained with human anti-LSA5 antibodies was also detected with anti-LSA5-antibodies from mice by IFAT on all *P. yoelii* strains tested (265BY strain, 17XNL strain and 17XNL clone 1.1). Western blotting of *P. yoelii* and *P. falciparum* sporozoite extracts yielded several bands ranging from 195 to 81 kDa (not shown), most likely reflecting the high Glu-rich content of the molecule.

In liver stages of *P. falciparum* and *P. yoelii* LSA5 expression could also be detected using human as well as mice antibodies (FIGS. 2-B and D). By IFA, LSA5 appears to be located in the parasitophorous vacuole of immature liver schizont (day 5) and distributed between the pseudocytomeres similarly to LSA1 (Fidock, Bottius et al. 1994), SALSA (Bottius, BenMohamed et al. 1996) and LSA3 (Daubersies, Thomas et al. 2000). Expression was seen in all liver-schizonts examined derived both from the NF54 strain obtained in chimpanzees, from the 3D7 clone derived from it, and from an African isolate used to infect the *Cebus appella.*

On asexual blood stages of *P. falciparum*, a cross-reactivity similar to that found with P.f. 11.1 has been observed with human and mouse antibodies to LSA-5, due to the high content of Glu-rich regions in both proteins. In contrast, the same human and mouse antibodies were found non-reactive with asexual blood stages of *P. yoelii* using asynchroneous material, i.e. containing all developmental stages.

The ultrastructural localisation of LSA-5 was revealed by immunogold labeling of a) sporozoites (FIGS. 3-A and B), where it is associated with the membrane but also abundant in the cytoplasm, and b) of fully mature liver forms, which showed the protein to be associated with the fluffy or flocculent material present in the parasitophorous vacuole which surrounds the emerging exoerythrocytic merozoites (FIGS. 4-A, B, and C). Notably, labelling of LSA-5 was always seen within the PVM (Parasitophorous Vacuole Membrane) and never in the hepatocyte cytoplasm nor on the hepatocyte surface. The intensity of the staining, both by IFAT and by EM indicates that LSA5 is actively synthesised during liver schyzogony.

The stage-specific expression of LSA-5 was indicated by the above experiments. It was confirmed by the reactivity of LSA5-71 with sera from 3 human volunteers immunised by irradiated sporozoites and who were protected upon challenge (hence by antibodies directed mainly to pre-erythrocytic stage antigens), as well as 2 other priests' sera (Sceur Neveu, and Pere Gouel, in addition to Pere Mauvais) and by sera from *P. yoelii* challenged mice undergoing treatment by pyrimethamine, which developed Abs only to sporozoite and liver stages (not shown).

Example 3

LSA-5 is Highly Antigenic in Individuals Exposed to Various Levels of Malaria Transmission The high prevalence of immune responses in humans was one of the further criteria of selection for LSA-5, after showing protection in mice, and conservation.

The prevalence was first evaluated on western blots of the recombinant protein Bgal-571 (LSA5) using 43 sera from individuals aged 2-75 years, living in Podor (Senegal), an area of very low endemicity (1-5 infective bites/year). Ab responses against LSA5 were detected in 91% of the individuals tested (not shown) thus showing its antigenicity as compared to 78% for PfEMP3 and 80% for SALSA (Bottius, BenMohamed et al. 1996) in the same individuals.

This intial indication was completed by further ELISA studies using sera from 328 individuals, of all age groups, living in two high transmission areas, that of Dielmo (Senegal) and Donse (Burkina Faso), and the low transmission area of Podor (Northern Senegal). Results are summarised in FIG. 5. Ab responses against the consensus peptide 571 were detected in all groups tested, with an increase in the prevalence of antibody responders as a function of age and of area, ie depending on the exposure and the level of. is transmission of the parasite (51.5% in Podor, 66% in Donse, and 75.5% in Dielmo)

In each area, there was an age dependant increase of both prevalence and titres of Abs particularly detectable among the younger subjects. The higher prevalence of the 0-5 years group as compared to 5-10 years being likely related to the small numbers in the second group (8 Vs 12). From one area to the other, there was a relationship between either the prevalence or the mean levels of specific IgG and the mean number of sporozoite inoculations. As shown in FIG. 2, IgG Ab responses increased with exposure to infected mosquitoe bites, with 17.5% of high responders in Podor, 33.5% in Donse, and 52% in Dielmo.

Results obtained in Podor, the lowest transmission area are again in favour of the high antigenicity of the native LSA5 since specific antibody responses can be elicited after very few malaria infective mosquito bites.

The prevalences recorded for LSA5 are therefore significantly higher than those previously recorded in the same subjects from the same areas for LSA1 (Fidock, Gras-Masse et al. 1994), Salsa (Bottius, BenMohamed et al. 1996), Starp (Fidock, Bottius et al. 1994), CS (Bottius, BenMohamed et al. 1996), PfEMP3 and EBA175. They are as high or higher than those recorded for LSA3 (Perlaza, Sauzet et al. 2001).

Example 4

Anti-LSA-5 Antibodies Strongly Inhibits *P. falciparum* and *P. yoelii* Invasion into Hepatocytes, Both Under in vitro and in vivo Conditions 4.1. In-vitro Results.

Having demonstrated the existence of shared B-cell epitopes between LSA5 and the two rodent malaria parasites *P. yoelii* and *P. berghei*, the effect of anti-LSA5 antibodies on in vitro invasion of murine hepatocytes by *P. yoelii* and *P. berghei* sporozoites was examined. Experiments using the two rodent species were conducted in parallel, i.e. performed using a single hepatocyte preparation (FIG. 6). Human antibodies immunopurified on LSA5-71 showed 99% inhibition of *P. yoelii* and 60% inhibition of *P. berghei* sporozoite invasion, respectively. The inhibition was 50% when antibodies where immunopurified on recombinant protein DG88 belonging to 11.1 antigen. The antibodies immunopurified on the non-cross-reactive antigen SALSA had no significant effect (<10% inhibition).

The nearly complete inhibition obtained with anti-LSA-5 antibodies is similar to that obtained with anti-LSA-3 (Bottius, BenMohamed et al. 1996), and stands among the highest ever obtained. Indeed, inhibition of sporozoite invasion has been obtained previously using anti-circumsporozoite protein monoclonal antibodies as well as human antibodies against STARP, SALSA, LSA-3. However, with anti-CS, STARP and SALSA, inhibition was sometimes strong but never total. It remained always a proportion of sporozoites able to transform into liver-stages. This is probably related to the target antigen, as it occurred whatever the antibody concentration tested which were as high as 1 g per liter for anti-CS Mab, whereas the LSA-3 and LSA-5 results were gathered using affinity-purified antibodies, i.e. at relatively modest antibody concentration, titrating 1:2 to 1:100 on sporozoite surface (whereas anti-CS Mab at 0.5 g/l had a titer of $1 \times 10^7$).

Invasion Inhibition of *P. Falciparum* Sporozoites into Human Hepatocytes:

Human affinity purified anti-LSA-5-71 and antibodies raised in mice, adjusted at an IFAT endpoint titre of 1/50 were added, together with *P. falciparum* sporozoites to human hepatocytes primary cultures. In preliminary experiments performed in duplicate, a 95% inhibition of invasion was obtained with human Abs. The specificity of the effect of the antibodies was ascertained by reversion of the inhibitory effect, by addition of the LSA-5-71 to antigen at a concentration of 10 µg/ml. In control wells, the antigen had no inhibitory effect by itself, and when added to the anti-LSA-5-71 human antibody, it totally reversed the invasion inhibition observed, thereby indicating clearly that the inhibitory effect was due to the paratope, the antigen binding site of the antibody, ie. not to any kind of toxic effect linked with the antibody preparation. Moreover, in the wells with anti-LSA-5-71 antibodies the remaining sporozoites were agglutinated, i.e. likely by the antibody, and this was reversed by the antigen. Antibodies raised in mice had a much weaker effect than human affinity-purified antibodies (45%). The anti-Circum-Sporozoite protein 2A10 Mab was employed as positive control, and an antibody against DG536 (LSA-1), not expressed on the sporozoite, as negative control. Since those results have been obtained recently and deserve to be repeated in another experiment, they are not shown.

4.2. In-Vivo Results: Passive Transfer Experiments.

The in vitro invasion inhibitions were confirmed by in vivo studies. The human affinity-purified anti-DG571 antibodies were tested in passive transfer experiments. Human anti-DG729 (LSA3 Nterm) antibodies for which the protective effect against *P. yoelii* sporozoite infection has been shown previously was used in parallel as positive control. Two mice per group were tested. In each group, mice were injected with sporozoites mixed together with the specific antibody. A group of negative control included mice injected with sporozoites together with anti-SALSA antibodies, that does not react with *P. yoelii* sporozoites, whereas a last group of mice received sporozoites alone to check parasite infectivity. From day 4 to day 21 post-inoculation, no parasites could be detected in mice that had received anti-LSA5 antibodies indicating that human anti-LSA5 antibodies had fully protected mice against *P. yoelii* sporozoite infection. In contrast, control mice that had received sporozoites pre-incubated with anti-SALSA antibodies, or untreated sporozoites had a patent parasitaemia from day 5 and the infection followed a normal course (Table 3). It should be to underscored that, in contrast with passive experiments performed using monoclonal Abs anti-TRAP or anti-CSP of *P. yoelii*, where huge amounts of antibodies had to be transferred, respectively 500 µg (Gantt, Persson et al. 2000), and 1 mg (Charoenvit, Mellouk et al. 1991), the anti-LSA-5 antibodies were protective at a much lower amount (20 µg).

TABLE 3

In vivo protective effect of anti-LSA5 Abs in passive transfer experiments. 100 µg/ml of human anti-LSA5, anti-βgal-DG729 (LSA3) or anti-βgal-DG671 (SALSA) Abs were added to 150 *P. yoelii* sporozoites, in a final volume of 200 µl/mouse, and injected into the tail vein of Balb/C mice. Parasitemia were recorded from day 4 to day 21 after challenge.

| Ab | Sporozoite IFAT | | N° infected/tested | | |
|---|---|---|---|---|---|
| | P. f | P. y | $1^{st}$ exp | $2^{nd}$ exp | Total |
| Anti-LSA-5 | + | + | 0/2 | | 0/2 |
| Anti-βgal-DG729 | + | + | 0/2 | 0/2 | 0/4 |
| Anti-βgal-DG671 | + | − | 2/2 | 2/2 | 4/4 |
| None | | | 2/2 | 2/2 | 4/4 |

Example 5

Immunisation with LSA-5 Induces Protection against a *P. yoelii* Sporozoite Challenge in Several Strains of Mice Low Dose Sporozoite Challenge.

In the first experiment, 3 strains of mice (C57BL/6, BALB/c and F1(C57BL/6xBALB/c)) received four immunisations of either βgal-DG571 (LSA5) or βgal-DG671

(SALSA), and were challenged by intravenous inoculation of 10.000 *P. yoelii* sporozoites (17XNL strain).

4/5 (80%) of C57BL/6 inbred mice, 4/5 (80%) of BALB/c and 14/16 (87%) of outbred mice F1: (C57BL/6XBALB/c) showed a significant degree of protection (FIG. 7).

2 of the five C57BL/6 (40%) had sterile protection whereas in 2 other mice, parasitemia was delayed by 3 days compared to mice from control group (corresponding to a mean 99.2% reduction in intra-hepatic parasite burden). Four of five LSA5 immunised BALB/c mice were partially protected, showing a 48 h delay in the emergence of the parasitemia. 5 of five outbred mice showed partial protection, 2 mice being delayed by 3 days and 3 by one day. In a second experiment partial protection was further confirmed in nine of eleven outbred mice (81%), 5 mice being delayed by 3 days and 4 by 2 days. In contrast, the onset of blood parasitemia occurred at day 5 post-challenge, ie. without delay, in all 31 control mice immunised with the antigen ⊖gal-DG671 (SALSA), and 20 control non-immunized mice.

In the third experiment 5 C3H/HeJ and 5 BALB/c mice were immunised with 50 μg of the LSA5 recombinant GST-DG 571, adsorbed on polystyrene beads and were subsequently challenged, together with 5 GST controls with 500 live *P. yoelii* sporozoites (17XNL clone 1.1) which is consistently infective at a rate of 100 sporozoites per animal. All 5 C3H and 5 BALB/C mice showed protection, full in two and partial in the remaining immunised mice.

Genetic immunisation was attempted but provided only a more modest 24 h delay in patency in each of the 8 immunised animals as compared to 9 controls.

High Doses Challenges with LS Enumeration.

The rate of the protection was subsequently investigated using a high sporozoite inoculum followed by in situ studies of the infected liver. As shown in FIG. 8, a strong reduction of the number of resulting liver schizonts was observed in all 4 strains of mice immunised with LSA5 ranging between 82 to 98.2% inhibition as compared to controls.

A 98.2% reduction in the number of liver schizonts was obtained in BALB/c, 95% in C57BL/6 and 82% in F1: (C57BL/6xBALB/c) mice. In addition full protection was obtained in 2/2 CD1 mice, immunised by LSA5-71 with CFA. These levels of protection are as high as those obtained previously in LSA3-immunised mice (Sauzet, Perlaza et al. 2001).

In Situ Observations.

Immunisation with LSA5 not only led to a profound decrease in the total number of liver forms upon high dose challenge, it was also associated with strong cellular defences in situ, around the parasite, in the liver (FIG. 9). Healthy liver forms were observed in the liver of control F1: (C57BL/6xBALB/c) mice receiving 1 million sporozoites (FIG. 9-A). Conversely, in animals immunised with LSA5, the liver was infiltrated by lympho-mononuclear cells with the presence of rare cell granuloma, consisting mostly of lymphocytes and macrophages where no intact liver form could be seen, but parasite antigen could be detected (revealed by an anti-LSA3 specific Ab) (FIG. 9-D). In some instances the liver form was still morphologically visible, but altered and infiltrated by leukocytes (FIG. 9-B, C).

*P. yoelii* low dose challenge experiments can only be interpreted by contrasting them with the reproducibility of emergence of parasite in the blood, ie. the time to maturation of LS, in control antigen or control adjuvant mice, challenged simultaneously. It was previously described that no delay was observed amongst >100 control mice (Sauzet, Perlaza et al. 2001), and recently calculated that in over 300 control mice a maximal delay of 24 hours had been observed in less than 3% of cases. That only partial protection is frequently obtained may not be surprising: mice are immunised with a *P. falciparum* molecule, challenged by *P. yoelii*, which contains a homologous cross-reactive molecule. The number of epitopes shared between the two species being less, therefore full, sterile, protection is more difficult to achieve since the target antigen is not identical and likely contains only limited epitope similarities. In experiments where various numbers of sporozoites for challenge were used, a 1, 2, 3, days delay in parasitemia was found to correspond respectively to 80, 96 and 99.2% reduction in parasite burden (Sauzet, Perlaza et al. 2001). The extent of protection that was evaluated in situ after high dose challenge, where the actual reduction in the total number of liver forms per animal was measured precisely, are actually in agreement with these figures.

Figure 16:
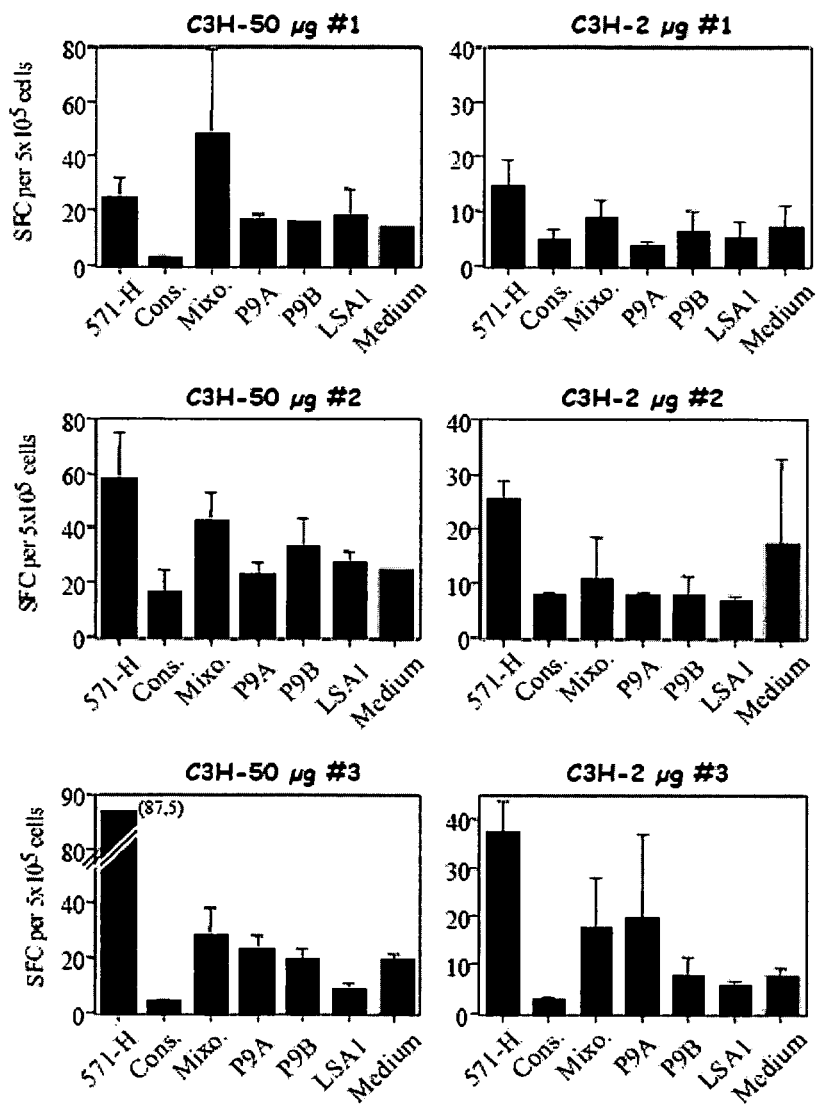

Recent results confirm the very high immunogenicity of LSA-5, particularly that of microparticulate formulations without adjuvant. In two breeds of mice, namely C3H or Balb/C, immunisations were performed by subcutaneous inoculations, without adjuvant, of polystyren microparticles coated with LSA-5-DG571 protein. High level proliferative responses, antibody responses and IFN-gamma secretion were obtained in all animals at all doses, in both breeds of mice. FIGS. 15 and 16 show in particular the secretion of Interferon-gamma measured by Elispot assay which is correlates best with the status of protection. Results show a greater dose dependence of results in Balb/C as compared to C3H. At the highest dose, the number of responding cells was very high, ranging from 100 to 250 spots per million PBMC, in response to the 571-histidine recombinant protein and/or to the consensus 571 LSA-5 peptide, the mixotope LSA-5, far less to P9A and P9B peptides derived from the 11.1 published sequence or to control antigens such as LSA-1.

Finally, in situ investigations in the liver showed a very strong recruitment of T-lymphocytes around the LSA5 antigen, indicating that specific lymphocytes could migrate and home in this location Altogether, these results show that very low to medium doses of antigen delivered in microparticulate form without adjuvant can induce very strong immune responses, particularly those found previously to be related to a state of protection in mice, in non-human primates or in humans.

Example 6

Immunisation of Aotus Monkeys with LSA-5 without Adjuvant Indicates that LSA-5 Can Induce Protection against a *P. falciparum* Challenge Three out of 4 Aotus immunised with DG 571 recombinant protein adsorbed onto microparticules were completely protected after challenge with sporozoites from Santa Lucia strain (FIG. 10-C). By contrast, the three Aotus immunised with control Ag (FIG. 10-A) and two non-immunised animals (FIG. 10-B) developed patent *P. falciparum* parasitemia detectable from day 0 to 10. All Aotus received drug treatment at day 60.

Among the LSA-5 immunised group, three monkeys (M217, M219 and V86) presented no parasitemia whatsoever at any time point during the 40 days of the follow-up, while the remaining one (M221) developed patency on a single day (day 13) only. Parasitemias in the control group and in the two immunised not-protected Aotus were moderate, ranging from 71 to 500 parasites/μl. All Aotus received drug treatment at day 60.

Although results are still preliminary they nevertheless represent the second report of a malaria pre-erythrocytic subunit vaccine candidate capable of inducing protection in Aotus monkeys against *P. falciparum* sporozoite challenge, and in this case with heterologous strain challenge. The results suggest a protective effect of LSA5 in immunised monkeys.

Previous trials conducted in Aotus with other pre-erythrocytic Ags such as CS or Spf 66 had so far failed to induce protection after challenge with *P. falciparum* sporozoites, except for LSA3 (Perlaza, Zapata et al., 2003). Importantly, in view of the high polymorphism reported in other malaria vaccine candidates, protection afforded by the LSA-5 protein derived from the T9-96 clone extended to challenge by the Santa Lucia strain. This is in agreement with the high degree of LSA-5 sequence conservation across parasite isolates reported above.

Example 7

Protection Induced by LSA5 is Associated with Elevated IFN-γ Responses

IFN-γ was considered here for two reasons: first, because it is established as a major mediator of protection against malaria liver stages, and second because it is a more reliable index of T cell activation than proliferation assays which are particularly difficult with Aotus lymphocytes (Perlaza, Zapata et al. 2003).

IFN-γ in the supernatants: IFN-γ production by cells from all LSA-5 immunised monkeys was specifically induced by the recombinant protein DG-571 (FIG. 11). Levels were comparable to those specifically produced in LSA-3 immunised animals (Perlaza, Zapata et al. 2003). Importantly, IFN-γ secretion by PBMC was also induced in response to *P. falciparum* sporozoite extracts, indicating that the native epitopes in LSA-5 were well processed and recognised by the vaccine-stimulated cells. The specificity of IFN-γ production was demonstrated by negative results obtained from the 3 control monkeys tested in parallel, as well as with cells obtained before immunisation (not shown).

ELISPOT: Only cells from 3 immunised Aotus could be studied by this technique (for quantitative reasons). The frequency of IFN-γ producing cells ranged from 62 to 190/1×10⁶ PBMC in response to the recombinant protein (FIG. 12). It is noteworthy that the only non-protected Aotus M221, showed the lowest responses to LSA-5, and more importantly did not respond at all to the LSA-5 derived synthetic peptide used in the same assay. In contrast, the other two animals studied had significant responses to the peptide. Finally, no LSA-5 specific IFN-γ producing cells could be detected in any of the three GST-immunised control Aotus.

All three protected Aotus immunised with LSA-5 were able to mount IFN-γ specific T-cell responses to LSA-5. For the non-protected animal, there was a significant signal in supernatants and not by Elispot. However, it should be noted that this animal had only a single day parasitaemia, ie. might be partially protected and second that the IFN-γ titers were determined two months before the challenge.

Conversely, specific Abs were hardly detectable. By Elisa they were absent from all animals except one (M217, see Table 4), and by IFAT they were present at significant levels (threshold of positivity 1/100) but at low to medium titres (1/200 to 1/800, Table 4). This immune response profile, made of high IFN-γ responses and low antibodies is typical of the profile related to protection. It has been previously observed using LSA3 delivered in similar manner both in mice and in Aotus (Perlaza, Zapata et al. 2003), as well as after genetic immunisation both in mice (Sauzet, Perlaza et al. 2001) and in chimpanzees, and is also quite close to that obtained with lipopeptides without adjuvant where strong T-cell responses were dominant (BenMohamed, Gras-Masse et al. 1997; Perlaza, Arevalo-Herrera et al. 1998).

TABLE 4

Antibody responses.

| Aotus | Antigen | ELISA titer[a] | Spz IFA titer[b,c] |
|---|---|---|---|
| V85 | GST | <100[d] | 400 |
| | 571-GST | <100 | |
| | 571 petide | <100 | |
| | P9B peptide | <100 | |
| V86 | GST | <100 | 400 |
| | 571-GST | <100 | |
| | 571 petide | <100 | |
| | P9B peptide | <100 | |
| M217 | GST | <100 | 800 |
| | 571-GST | 350 | |
| | 571 petide | <100 | |
| | P9B peptide | 240 | |
| M219 | GST | <100 | 200 |
| | 571-GST | <100 | |
| | 571 petide | <100 | |
| | P9B peptide | <100 | |
| M221 | GST | <100 | 400 |
| | 571-GST | <100 | |
| | 571 petide | <100 | |
| | P9B peptide | <100 | |

[a]Elisa titers were determined in samples taken 140 days after the third immunization. Titers correspond to the dilution of the test sera whose optical density at 450 nm was the mean of 10 control *Aotus* sera plus 2SD.
[b]IFA, indirect immunofluorescence assay. Data are expressed as reciprocal endpoint dilutions.
[c]IFA titers on of sera at day 40 after the third immunization.
[d]Negative at a dilution 1:100

Example 8

Co-Immunisation with LSA-3 and LSA-5 Indicates that Both Molecules are Immunogenic when Presented Together Since LSA5 is one of the very rare antigens able to induce a protection against sporozoite challenge, combined immunisations of LSA3+LSA5 were performed, as compared to single immunisation in a same batch of mice. In mice immunised with each recombinant protein individually, strong specific antibody responses were induced at the highest dose. At a dose as low as 1 μg, both proteins were still highly immunogenic (FIG. 13). However, whereas anti-LSA-3 Ab titres did not differ significantly compared to the higher dose, anti-LSA-5 titres were two to three folds lower. When both antigens were combined, ie. injected together in the same syringe, the immunogenicity of each was preserved even at low dose and antibody titres to each protein in those mice were independent of the dose. Particularly interesting is the fact that mice immunised with low doses of LSA-3+LSA-5 exhibited anti-LSA-5 antibodies 3 orders of magnitude higher than in mice immunised with LSA-5 alone, bringing titres to levels similar to those immunised at high doses. These results tend to indicate that associating both antigens is beneficial at the immunological level, at least in terms of Ab responses since anti-LSA-5 Ab responses can benefit some help from anti-LSA-3 specific responses, even when not covalently associated.

The inventors have observed previously that when combining antigens the immunogenicity of each frequently decreased. For instance the immunogenicity of LSA1 was markedly decreased when it was associated with the circumsporozoite protein (Londono, Gras-Masse et al. 1990). The same occurred when RTS'S was associated with TRAP and the protection is seen with RTSS alone was lost. In chimpanzee the association of LSA3 with either Starp, Salsa or LSA1 led to both a marked decrease of IFN titers to LSA3 and the protection induced by LSA3 alone was lost (unpublished material). Therefore the absence of negative interference between LSA3 and LSA5, and moreover the increase in immunogenicity recorded are very positive and rather unusual findings.

Discussion

The stage specificity of LSA5 was demonstrated by reactivity of human, mice and Aotus antibodies to the sporozoite surface and to liver stages, both by IFAT and EM, as well as by invasion inhibition both in vitro and in vivo. The identification of LSA5 extends the range of molecules that can be targeted by Abs on the *P. falciparum* sporozoite surface. Moreover, LSA5 being expressed in both sporozoites and liver stages can be targeted by both humoral and cellular defence mechanisms.

In contrast with other pre-erythrocytic vaccine candidates, such as CSP and TRAP, LSA-5 is very well conserved as the dominant epitopes could be detected in 32 isolates at sporozoites stage generated from patients gametocytes. This is obviously a critical characteristic since antigen polymorphism has been repeatedly stressed to be a major limitation to vaccine development (Facer and Tanner 1997). It is important to underscore that the challenges were performed using an heterologous parasite in Aotus, the Santa Lucia strain, whereas the vaccine formulation was based on the gene sequence obtained from the T9-96 clone. This strongly contrasts with other malaria vaccine candidates, where polymorphisms are known to be present and limiting protection, and therefore where challenges have to rely on the homologous strain (Kwiatkowski and Marsh 1997).

The antigenicity of the molecule was found to be very satisfactory. Specific antibodies were detected at high prevalence in 3 endemic areas. Prevalence was as high or higher than that of other pre-erythrocytic stages candidates such as LSA1, SALSA, STARP and CS (Fidock, Bottius et al. 1994; Fidock, Gras-Masse et al. 1994; Bottius, BenMohamed et at 1996) (and that of many asexual blood stages antigens), this being particularly clear in the case of the lowest malaria transmission area studied. With an average 1-5 infective mosquitoe bites per person in Podor and an average 10 sporozoites delivered by each bite, the proportion of responding children in the 0-5 and 5-10 years age groups who have therefore received an average 50-250 and 100-500 parasites in total, is amazingly high. The comparison of data from the 3 different areas studied and the age pattern of response indicates that the immune responses are a function of exposure to infected mosquito bites.

Indications in favour of protection were obtained by in vitro studies, both with *P. yoelii* and *P. falciparum*, by passive transfer of antibodies in vivo, by challenge of immunised mice by *P. yoelii* sporozoites, and by challenges of immunised Aotus primates by *P. falciparum*.

As concerning the in vitro inhibition, its Ag-specificity was ascertained by reversion of the Ab effect in the presence of an excess of Ag. Beside the use of human hepatocytes which is the only host cell able to produce reliable results (Mellouk, Berbiguier et al. 1990), this procedure of reversal has not been used for other invasion-inhibition assays performed either for blood or liver forms by other research groups. It is however probably the most reliable is means to show its antigen-specificity.

Concerning the *P. yoelii* in vivo model, it is important to insist on the high stringency of this model for the following reasons: i) mice are highly susceptible to sporozoite infection since as few as 100 sporozoites injected can induce blood infection. ii) the recombinant proteins used for the immunisation are derived from human malaria *P. falciparum* parasites, whereas the parasite used for challenge is the rodent *P. yoelii* species. Therefore the protection observed relies upon a limited number of shared epitopes between these two species. The percent protection measured after high dose challenges are in full agreement with the estimated reductions based on delay of emergence of parasitaemia. Further in situ investigation also highlighted that lymphocyte recruitment is a major defence mechanism responsible for protection. A technique was recently described (Hebert, Sauzet et al. 2003) designed to analyse the epitope-specific cell recruitment in the liver, where peptide-coated polystyrene beads are injected intra-portally in recombinant-immunised mice. This technique, validated using LSA3-derived peptides (Hebert, Sauzet et al. 2003), was further used to compare cell recruitment induced by immunisation protocols either able to induce protection or not (using distinct adjuvants). It was also employed in LSA5.71 immunised mice receiving intra hepatic particles coated with the LSA5 consensus peptide. This induced a strong peptide specific cell recruitment around test and not around control beads (not shown), essentially similar to that seen around challenge parasites reported (FIG. 9-D), and made mostly of CD3, CD4, CD8, NK cells and macrophages. to Although antibodies were found to play a clear role, these in situ investigations strongly suggest that cellular mechanisms, particularly T-cells able to secrete high levels of IFN-γ and to migrate towards the intra-hepatic schizont, play the most important role.

Results obtained in Aotus monkeys suggest that LSA-5 is one of the very rare candidates that can achieve protection against a *P. falciparum* sporozoite challenge. Indeed, there are several molecules that have induced immunity in mice against rodent malaria challenge, CS, TRAP and combinations of the two, being the most studied (Schneider, Gilbert et al. 1998). Conversely, there are very few molecules that have shown a protective effect against a *P. falciparum* challenge in primates or in humans. This has been achieved to-date only by LSA-3 and LSA-5 against both homologous and heterologous strain challenges and, to a more limited extent and for shorter time, by RTSS, a particulate formulation of CS (Stoute, Slaoui et al. 1997). These results are in contrast with those previously obtained in humans or in higher primates with other characterised molecules, which have proved unable to achieve the same degree of protection, namely LSA-1, TRAP, SALSA, STARP, PfEXP1, SpF66.

It is remarkable that protection could be obtained by using very low doses of antigen, by a delivery system that does not require the use of any powerful nor toxic adjuvant. These results were expected since this mode of immunisation was found to induce preferentially T cell responses that were associated with protection in previous experiments in mice, and low immunizing doses of antigen were found more effective than high doses (Sauzet et al in preparation). Although the number of primates, which are rare, precious and expensive animals, that can be enrolled, does not allow us to reach statistical significance, the reproducibility of the challenges in Aotus by sporozoites of the Santa Lucia strain has been established previously in more than 11 infections (Zapata, Perlaza et al. 2002) and is confirmed by results obtained in the 5 controls employed here and in 4 employed in a previous study (Perlaza, Zapata et al. 2003). It is noteworthy that the mode of immunisation successfully employed here in mice and in primates is the same as that previously found successful in mice and in Aotus with LSA-3, and produced similar type of responses and protection in both species (Perlaza, Zapata et al. 2003).

IFN-γ is the most potent cytokine active against the LS development (Ferreira, Schofield et al. 1986; Mellouk, Maheshwari et al. 1987; Schofield, Ferreira et al. 1987). Results tend to confirm that specific IFN-γ secretion by PBMC is an important component of defence against *P. falciparum* pre-erythrocytic stages, at least by Elispot in the present study. Specific IFN-γ secretion obtained in response to the sporozoite native protein suggests a proper processing of both natural and "artificial" epitopes for presentation to T cells, i.e. a proper conformation of the immunogens. These results are in-keeping with previous data obtained with another vaccine candidate, LSA-3, both in chimpanzees and in Aotus. Indeed, the high IFN-γ and low antibody responses, associated with LSA-5 induced protection, both in mice and in primates, are surrogates essentially similar to those previously recorded in LSA-3 experiments (BenMohamed, Gras-Masse et al. 1997; Benmohamed, Thomas et al. 2000; Daubersies, Thomas et al. 2000). They are also similar to those recorded in mice and chimpanzees immunised by means of irradiated sporozoites (Druilhe et al, 1998, Doolan et al JI, and unpublished material). There is therefore a convergence in the available markers of protection in the 3 situations, which may be taken as an indirect indication that protection may be mediated, in those 3 situations, by the same effector mechanism.

Within the limitations of available models for challenge by human malaria sporozoites, LSA-3 and LSA-5 appear today as 2 very promising candidates, which are most antigenic and immunogenic, non-toxic and with demonstrated efficacy, though never in all animals immunised. The development of combined vaccines probably implies to combine candidates with proven efficacy, which is the case, at pre-clinical level, for both LSA-3 and LSA-5. Moreover it is shown here that combined immunisation with LSA-3 and LSA-5 provided an improvement, particularly of LSA5 responses. It seems therefore valuable to investigate whether, by combining an attack on 2 distinct antigenic targets, improved protection can be achieved.

Example 9

Experimental Protocol to Test whether a Peptide or Polypeptide is Recognized by Anti-LSA5 Specific Antibodies A typical experimental protocole is an ELISA assay, such as that described in the above materials and methods, in which the test peptide used in place of the LSA-5 71 consensus peptide described in this ELISA method, and the antibody directed to the consensus peptide or to any other of the sequence described in table 1, is used to test its reactivity with a test peptide (using either human affinity purified antibodies on the consensus peptide or sera from animals immunised with the consensus peptide with an appropriate adjuvant, such as Montanide ISA720 or Freund complete adjuvant).

Another way of assessing whether a peptide or polypeptide is recognised by LSA-5 specific antibodies is to use the procedure described in relation to the disclosure of FIG. 13 above, this time with coating with a consensus peptide and where the test peptide is used in a competition assay mixed at various concentrations ranging from 10 microgrammes to 1 mg per ml to the test antibody, so as to determine whether it can inhibit the binding of the antibody to the consensus peptide.

The same type of procedure can be employed if the peptide is linked to nitrocellulose surface in an immuno-blotting experiment or, finally, if the test peptide is used in an IFAT inhibition assay similar to that described above with the ELISA, where the test peptide is mixed with an anti-consensus sequence antibody and used to inhibit the binding to the parasite in an IFAT assay.

Example 10

Additional Data about Protection against Pre-Erythrocytic Stages

I.1—Recognition of LSA-3 and LSA-5 by the Sera of Human Volunteers Immunised by Irradiated Sporozoites These experiments were performed in order to reach 2 goals: a) indirectly confirm the expression, during the pre-erythrocytic stages, namely sporozoite and the liver stage, of those 2 molecules by showing an immune response in individuals who have not harboured the erythrocytic stages of *Plasmodium falciparum*. and b) evaluate the immunogenicity of the molecule as compared to others. Indeed, among the 120 gene fragments belonging to pre-erythrocytic stage molecules which correspond to ca. 39 genes, very few of them were recognised by immune responses developed by individuals immunised by irradiated sporozoites, despite the fact that these individuals are protected. This was the means actually used to identify LSA-3 initially, which was among the 120 gene fragments that which showed the strongest and most remarkable positivity with sera from individuals immunised by irradiated sporozoites of *P. falciparum*. For instance, other molecules that are strongly immunogenic under natural conditions of exposure, such as LSA-1, SALSA, STARP, PfEXP1, TRAP, are not recognised by sera from irradiated sporozoite protected volunteers. This was true also at T-cell level in Elispot assays performed with cells from 4 individuals immunised and protected by irradiated sporozoites.

ELISA assays were performed using 8 naive volunteers sera, which were used to define the threshold of positivity. This corresponded to the mean OD value given by the 8 negative controls+3 standard deviations. Test sera included 2 sera from priests who had been living for respectively 26 and 21 years under continuous daily prophylaxis by chloroquine (Pere Mauvais and Sceur Neveu), who had developed very strong responses to sporozoite surface antigens and liver stage antigens, though very little—if any—to blood stage molecules, and 4 sera communicated by the Naval Medical Research Institute from volunteers who underwent 12 to 14 immunisations by several hundred irradiated mosquitoes over a year and a half of immunisation and were protected upon challenge (sera V1-4). Sera were collected following immunisation before challenge.

The main results expressed in arbitrary units, or ratio of OD value of the test sera compared to the mean+3 SD of the controls, are summarised in the following table.

They show (table I) a specific antibody reactivity with the 2 molecules, LSA-3 and LSA-5, which indicate that contact with sporozoites and/or liver forms induced antibodies specific to those 2 molecules and moreover, as mentioned above, that those molecules are immunogenic under such conditions of immunisation, which distinguish them from most other pre-erythrocytic stage vaccine candidates developed so far, including the Circum Sporozoite Protein.

2—Association between Anti-LSA-5 IgG Responses and Protection against Infectious Mosquitoe Bites under Field Conditions.

In this study, we employed the set-up of Dielmo, Senegal, where extremely precise records of clinical malaria attacks were obtained by daily visits by medical doctors to each of the inhabitants, continuous access to the medical team—day and night—, detailed counting of parasite densities and the determination of an age-dependent pyrogenic threshold to precisely assign to a malaria attack any episode of fever, headache or other symptom which could be related to malaria in unequivocal manner.

Anti-LSA-5 total IgG antibody responses were determined by ELISA assays using the consensus LSA-5 peptide as coating antigen, used at a concentration of 10 microG/ml.

The antibody data was analysed by statistical analysis with the delay of blood repositivation following radical cure and natural exposure to infected mosquito bites. 95 of individuals of all age groups from the village of Dielmo received a radical cure by quinine at a rate of 25 mg/kg daily for 8 days, and daily blood smears were used to follow-up the delay of reappearance of blood stage parasites under continuous natural sporozoite challenges. This parameter is referred below to <<delay of repositivation>>.

In order to take into account the important confounding factors that are, for instance, age or protection afforded by the sickle-cell trait, glucose-6-phosphate deficiency, etc. . . . , we employed a multivariate stepwise regression analysis model where the influence of several variables are tested simultaneously, using the JMP software. The test of the null hypothesis was based on the variance ratio, denoted by F and departure from the null hypothesis tended to give values of F>1.

When the anti-LSA-5 antibodies were analysed together with several variables in the multivariate stepwise regression analysis, namely the delay of repositivation, age, haemoglobin type (AA or AS) G6PD deficiency, spleen rate, anti-blood stage IgG responses, the only significant associations were as follows:

The delay of repositivation increased with age (F ratio=4.22; P=0.042), decreased with spleen rates (F ratio=4.79; P=0.031), increased with anti-LSA-5 IgG responses (F ratio=4.16; P=0.044).

In other words, anti-LSA-5 antibodies had an effect on the transformation of sporozoites into liver forms and the emergence of blood forms, as strong as that of age.

Example 11

Evidences in Favour of Protection against Blood Stages

1: We then analysed the anti-LSA-5 antibody data together with the is occurrence of malaria attacks, which are due to the intra-erythrocytic stage of the parasite (observed during one year after blood sampling), age, haemoglobin (AA or AS), G6PD deficiency, spleen index, antibody response to blood stage extract. The same antibody data in the 95 individuals was used to analyse the association between the anti-LSA-5 antibodies and the protection from clinical malaria attacks during 1 year following the blood sample taken for the determination of anti-LSA-5 antibodies, by a multivariate stepwise regression analysis.

It was found that malaria attacks decreased as a function of age (F ratio=20.72; P<0.0001), are less prevalent in subjects with AS haemoglobin (F ratio=8.85; P=0.0037) and malaria attacks decreased as a function of anti-LSA-5 IqG response (F ratio=13.68; P=0.0004). Therefore, the protective effect of anti-LSA-5 antibodies is stronger than that conferred by the sickle-cell trait, which is well established as being one of the major genetic factors of resistance against malaria attacks.

2: in order to further the above analysis and include immune responses to other malarial antigens beyond total blood stage extract, a further analysis was performed in 155 individuals in whom was available the anti-LSA-5 antibodies, the occurrence of malaria attacks for 1 year, the age, the haemoglobin type, the G6PD deficiency, the anti-AMA-1 IgG response, the anti-MSP-1 IgG responses.

This analysis showed again, as expected, that malaria attacks decreased as a function of age (F ratio=23.43; P<0.001), that there was a trend of an increase in malaria attacks as a function of anti-MSP-1 IgG titres (F ratio 2.85; P=0.0093), and malaria attacks decreased as a function of anti-LSA-5 IgG responses (F ratio=18.98; P<0.0001).

is In other words, this analysis ruled out a protective effect of anti-blood stage extract antibodies, anti-AMA-1 antibodies, indicated with borderline significance an increased risk of malaria with increasing anti-MSP-1 antibodies (ie. a negative effect), and showed that anti-LSA-5 had a protective effect, which was extremely strong, as strong as that of age, which is well known in Dielmo as elsewhere to be a major variable of transformation between a state of susceptibility to protection against malaria attacks.

3 In vitro Studies: Parasite Killing, Evidence by the Antibody-Monocyte Cooperative Effect.

In view of the above immuno-epidemiological studies, there was evidence that anti-LSA-5 antibodies strongly reduce the number of malaria attacks. We therefore investigated the direct and indirect effects of anti-LSA-5 antibodies. Human antibodies employed in the passive transfer performed formerly in Thailand were used to prepare affinity-purified antibodies on the recombinant DG571.

The corresponding antibodies were found to have no direct effect upon the asexual blood stage parasite multiplication, e.g. no inhibition of merozoites invasion into red blood cells. Conversely, in the presence of normal blood monocytes, it was observed that anti-LSA-5 antibodies could cooperate with normal blood monocytes to produce parasite-killing factors that reduce the in vitro growth of *Plasmodium falciparum*. The study was performed three times together with controls, namely negative control IgG, positive control African IgG that can transfer protection into Thai children, and similar results were observed in each experiment: using affinity-purified antibodies titrating 1:200 which were employed diluted 10 times or diluted 20 times (i.e. at a final titre of 1:20 or 1:10 which are extremely low antibody concentrations), a strong parasite killing effect of either 78% (at 1:20 titre) or of 45% (at 1:10 titre) were reproducibly obtained.

This result indicates that anti-LSA-5 antibodies have a similar type of parasite killing effect as those described for anti-MSP-3 antibodies 4: Additional Studies Performed in Dielmo, Senegal, Demonstrate the Role of IgG3-anti-LSA5

In view of the above immuno-epidemiological and in vitro data, we investigated the role of various IgG subclasses in protection. Indeed only cytophilic subclasses of antibodies, gG1 and IgG3 can operate in the ADCI mechanism. Detailed studies led to determine the amounts of IgG1, IgG2, IgG3, and IgG4 anti-LSA-5 antibodies in 138 individuals from Dielmo.

Only the IgG3 subclass of anti-LSA-5 was found inversely correlated with the occurrence of malaria attacks (standard coefficient=−0.380; p=0.0003).

In a stepwise regression model of analysis, the association between a reduced number of malaria attacks and increased IgG3 anti-LSA-5 antibodies was confirmed with the F ratio=14.6 and a p value=0.0002.

Finally, using a nominal logistic analysis, this was again confirmed (LR chit=10.45; p=0.001).

5: Additional Studies Performed in Ndiop, Senegal

The same study was performed in the nearby village of Ndiop, where transmission is lower, in 90 individuals, aged 6 months to 92 years.

Again, in that population, an extremely strong association between protection against malaria attacks and the level of IgG3 anti-LSA-5 antibodies was observed: F ratio=27.53; p>0.0001, whereas this was not found for IgG1 anti-LSA-5 responses.

6: Additional Studies Performed in Kolle, Mali

In this study, which was primarily aimed at studying drug resistance of malaria parasites, it was observed that half of the cohorts of individuals harbouring parasites that are resistant to chloroquine could nevertheless clear their parasitemia and recover from malaria. 31 out of the 50 individuals tested were protected according to both parasitological and clinical observations. Patients able to clear their parasitemia had a significantly higher antibody titres to LSA-5 than those who did not and the same was true for MSP-3: in both cases, the strongest association was found for IgG3 anti-LSA-5 and IgG3 anti-MSP-3. Further studies of antibody response associated with decrease in parasite density showed a strong association for IgG3 anti-LSA-5 antibody titres and low parasite densities: F ratio=7.06; p=0.01).

7: Improved Survival of Cerebral Malaria Patients Harbouring IgG3 Anti-LSA-5 Antibodies Among 217 South East Asian malaria patients who had, for 108 of them, a cerebral malaria attack, and for 109 of them an acute uncomplicated malaria attack, there was no difference in antibody titres to total parasite extract, MSP-3, or LSA-5. These results are in agreement with results obtained previously in 4 other cerebral malaria cohorts.

The subgroup of 108 cerebral malaria patients were all treated with the most effective drug combination, namely artesunate-mefloquine. Analysis of antibody titres upon admission showed a significant difference on the outcome of drug-treated cerebral malaria depending on pre-existing antimalarial antibody titres in those patients: there was a significant improvement i.e. an increased survival was found in individuals having high IgG3 anti-MSP-3 antibodies or high IgG3 anti-LSA-5 antibodies (see below). is In contrast, control antibodies to other malaria vaccine candidates, such as anti-SERP-P126, or anti-AMA-1, were not related with the outcome of drug-treated cerebral malaria (no improvement was seen in the relation with antibody titres to those malaria vaccine candidates).

Thus, in total, the study strongly suggests that pre-existing anti-LSA-5 antibodies and anti-MSP-3 antibodies improve the survival rate which opens avenues for novel treatments of cerebral malaria, i.e. the association of antimalarial drugs with antibodies against LSA-5 and/or MSP-3 to improve the survival rate of drug-treated cerebral malaria patients.

In Conclusion, LSA-5 appears as one of the most promising vaccine candidates, with two major targets, one on pre-erythrocytic stages the other on blood stages:

1. LSA5 is able to induce in mice, in Aotus monkeys and in humans protection against sporozoite challenge, and able to induce antibodies that block sporozoites entry into hepatocytes.

2. LSA5 is able to mediate a monocyte-dependent parasite killing under in vitro conditions and under in vivo conditions in humans exposed to malaria in many different set-ups and, in a manner, that protect against acute uncomplicated as well as complicated malaria.

In one of the most detailed set-ups where clinical malaria has been extremely precisely documented, anti-LSA-5 IgG3 responses appear as one major, highly significant, factor of acquired resistance to clinical malaria. The type of statistical analysis employed controls for the effect of possible confounding factors, among which age and haemoglobin type are major ones, and clearly show an influence of a given antibody specificity, that directed to LSA-5 on acquired protection against malaria as compared to other antibody responses which are not found to be associated with protection.

Characteristics of 217 South-East Asian malaria patients
Indications obtained by univariate analysis:

|  | Mean ± StdD | 95% Confidence Interval |
| --- | --- | --- |
| Age (years) = | 37.5 ± 14.9 | [35.4-39.5] |
| rIgG1-P.f. = | 8.915 ± 5.721 | [8.149-9.681] |
| rIgG3-P.f. = | 13.798 ± 9.204 | [12.567-15.031] |
| rIgG1 MSP3-Cterm = | 12.097 ± 12.490 | [10.426-13.769] |
| rIgG3 MSP3-Cterm = | 15.738 ± 16.322 | [13.554-17.922] |
| rIgG1 MSP3b = | 1.760 ± 1.600 | [1.546-1.974] |
| rIgG3 MSP3b = | 4.358 ± 4.872 | [3.707-5.008] |
| rIgG1 LSA5 = | 11.513 ± 5.039 | [10.841-12.183] |
| rIgG3 LSA5 = | 12.993 ± 11.311 | [11.483-14.503] |

Comparaison of 108 patients with cerebral malaria
versus 109 patients with acute malaria attacks:

|  | Cerebral malaria | Acute attack |
| --- | --- | --- |
| Age (years) = | 37.8 ± 14.5 | 37.1 ± 15.4 |
| rIgG1-P.f. = | 9.05 ± 5.68 | 9.97 ± 5.99 |
| rIgG3-P.f. = | 14.59 ± 9.52 | 13.72 ± 9.09 |
| rIgG1 MSP3-Cterm = | 12.65 ± 13.23 | 12.61 ± 12.50 |
| rIgG3 MSP3-Cterm = | 15.85 ± 15.31 | 17.21 ± 18.37 |
| rIgG1 MSP3b = | 1.72 ± 1.46 | 1.93 ± 1.85 |
| rIgG3 MSP3b = | 4.62 ± 5.08 | 4.35 ± 4.93 |
| rIgG1 LSA5 = | 11.66 ± 5.10 | 11.76 ± 4.95 |
| rIgG3 LSA5 = | 14.59 ± 10.52 | 12.80 ± 12.32 |

There was no major indication of detectable differences in age or antibody responses between patients with cerebral malaria and patients with acute malaria attacks (when tested by univariate analysis)

Comparison of data obtained with regard to the outcome
in the subgroup of 108 cerebral malaria patients*:

|  | Death (N = 33) | Survival (N = 75) | Mann-Whitney U - test |
| --- | --- | --- | --- |
| Age = | 40.6 ± 14.8 | 36.5 ± 14.3 | p = .087 |
| rIgG1-P.f. = | 7.69 ± 4.96 | 9.70 ± 6.01 |  |
| rIgG3-P.f. = | 12.31 ± 9.44 | 15.52 ± 9.33 | p = .052 |
| rIgG1 MSP3-Cterm = | 8.88 ± 6.78 | 14.11 ± 14.89 |  |
| rIgG3 MSP3-Cterm = | 10.04 ± 10.43 | 18.17 ± 16.36 | p = .003 |
| rIgG1 MSP3b = | 1.42 ± 0.65 | 1.84 ± 1.67 |  |
| rIgG3 MSP3b = | 2.73 ± 1.59 | 5.40 ± 5.80 | p = .002 |
| rIgG1 LSA5 = | 11.46 ± 5.87 | 11.76 ± 4.91 |  |
| rIgG3 LSA5 = | 11.10 ± 8.65 | 16.04 ± 10.94 | p = .0155 |

(*= The patients did not receive a significantly different treatment).
A trend for a slight increase in mean age was observed in patients with deleterious evolution.

Indications Obtained by Multivariate Analysis:
When controlling for age, the risk of cerebral malaria (compared to that of acute uncomplicated malaria) was found reduced when rIgG3-LSA5 responses where high:
L-R chisquare=7.65; p=0.0057.
The outcome (death versus survival) was then tested in the subgroup of cerebral malaria patients with regard to both age and antibody responses.

The outcome was significantly improved (an increased occurence of survival was found), when rIgG3-MSP3-Cterm, or rIgG3-MSP3b or rIgG3-LSA5 were elevated. The relative "benefit" (=decreased occurence of death) of high IgG3-specific responses (when antibody responses were tested individually) was as follows

| | | |
|---|---|---|
| For IgG3-MSP3Cterm, | L-R chisquare = 7.41; | p = .0065 |
| For IgG3-MSP3b, | L-R chisquare = 10.70; | p = .0011 |
| For IgG3-LSA5, | L-R chisquare = 6.047; | p = 0.0139 |

TABLE I

| Test sera | LSA-3 NR2 | LSA-5 (His-6-5.71) |
|---|---|---|
| Père Mauvais | 2.8 | 1.9 |
| Sœur Neveu | 1.8 | 1.95 |
| Irr-spz.V.1 | 3.8 | 3.0 |
| Irr-spz.V.2 | 2.6 | 1.65 |
| Irr-spz.V,3 | 3.4 | 1.48 |
| Irr-spz.V.4 | 2.3 | 2.2 |

REFERENCES

BenMohamed, L., H. Gras-Masse, et al. (1997). "Lipopeptide immunization without adjuvant induces potent and long-lasting B, T helper, and cytotoxic T lymphocyte responses against a malaria liver stage antigen in mice and chimpanzees." *Eur J Immunol* 27(5): 1242-53.

Benmohamed, L., A. Thomas, et al. (2000). "High immunogenicity in chimpanzees of peptides and lipopeptides derived from four new *Plasmodium falciparum* pre-erythrocytic molecules." *Vaccine* 18(25): 2843-55.

Bouharoun-Tayoun H et al, 1990 J. Exp. Med. December 1990 1633-1641.

Bouharoun-Tayoun H et al, 1995 J. Exp. Med. August 1995 409-418

Bottius, E., L. BenMohamed, et al. (1996). "A novel *Plasmodium falciparum* sporozoite and liver stage antigen (SALSA) defines major B, T helper, and CTL epitopes." *J Immunol* 156(8): 2874-84.

Brahimi, K., E. Badell, et al. (2001). "Human antibodies against *Plasmodium falciparum* liver-stage antigen 3 cross-react with *Plasmodium yoelii* preerythrocytic-stage epitopes and inhibit sporozoite invasion in vitro and in vivo." *Infect Immun* 69(6): 3845-52.

Brahimi, K., J. L. Perignon, et al. (1993). "Fast immunopurification of small amounts of specific antibodies on peptides bound to ELISA plates." *J Immunol Methods* 162(1): 69-75.

Charlotte Gruner, A., G. Snounou, et al. (2003). "Pre-erythrocytic antigens of *Plasmodium falciparum*: from rags to riches?" *Trends Parasitol* 19(2): 74-8.

Charoenvit, Y., S. Mellouk, et al. (1991). "Monoclonal, but not polyclonal, antibodies protect against *Plasmodium yoelii* sporozoites." *J Immunol* 146(3): 1020-5.

Charoenvit, Y., S. Mellouk, et al. (1995). "*Plasmodium yoelii*: 17-kDa hepatic and erythrocytic stage protein is the target of an inhibitory monoclonal antibody." *Exp Parasitol* 80(3): 419-29.

Daubersies, P., A. W. Thomas, et al. (2000). "Protection against *Plasmodium falciparum* malaria in chimpanzees by immunization with the conserved pre-erythrocytic liver-stage antigen 3." *Nat Med* 6(11): 1258-63.

Deprez, B., H. Gras-Masse, et al. (1995). "Pimelautide or trimexautide as built-in adjuvants associated with an HIV-1-derived peptide: synthesis and in vivo induction of antibody and virus-specific cytotoxic T-lymphocyte-mediated response." *J Med Chem* 38(3): 459-65.

Druilhe, P., O. Pradier, et al. (1986). "Levels of antibodies to *Plasmodium falciparum* sporozoite surface antigens reflect malaria transmission rates and are persistent in the absence of reinfection." *Infect Immun* 53(2): 393-7.

Druilhe, P., R. M. Puebla, et al. (1984). "Species- and stage-specific antigens in exoerythrocytic stages of *Plasmodium falciparum*." *Am J Trop Med Hyg* 33(3): 336-41.

Facer, C. A. and M. Tanner (1997). "Clinical trials of malaria vaccines: progress and prospects." *Adv Parasitol* 39: 1-68.

Ferreira, A., L. Schofield, et al. (1986). "Inhibition of development of exoerythrocytic forms of malaria parasites by gamma-interferon." *Science* 232(4752): 881-4.

Fidock, D. A., E. Bottius, et al. (1994). "Cloning and characterization of a novel *Plasmodium falciparum* sporozoite surface antigen, STARP." *Mol Biochem Parasitol* 64(2): 219-32.

Fidock, D. A., H. Gras-Masse, et al. (1994). "*Plasmodium falciparum* liver stage antigen-1 is well conserved and contains potent B and T cell determinants." *J Immunol* 153(1): 190-204.

Galey, B., P. Druilhe, et al. (1990). "Evidence for diversity of *Plasmodium falciparum* sporozoite surface antigens derived from analysis of antibodies elicited in humans." *Infect Immun* 58(9): 2995-3001.

Gantt, S., C. Persson, et al. (2000). "Antibodies against thrombospondin-related anonymous protein do not inhibit *Plasmodium* sporozoite infectivity in vivo." *Infect Immun* 68(6): 3667-73.

Gras-Masse, H., J. C. Ameisen, et al. (1992). "Synthetic vaccines and HIV-1 hypervariability: a "mixotope" approach." *Pept Res* 5(4): 211-6.

Gruner, A. C., K. Brahimi, et al. (2001). "The *Plasmodium falciparum* knob-associated PfEMP3 antigen is also expressed at pre-erythrocytic stages and induces antibodies which inhibit sporozoite invasion." *Mol Biochem Parasitol* 112(2): 253-61.

Hebert, A., J. P. Sauzet, et al. (2003). "Analysis of intrahepatic peptide-specific cell recruitment in mice immunised with *Plasmodium falciparum* antigens." *J Immunol Methods* 275(1-2): 123-32.

Hurtado, S., M. L. Salas, et al. (1997). "Regular production of infective sporozoites of *Plasmodium falciparum* and *P. vivax* in laboratory-bred *Anopheles albimanus*." *Ann Trop Med Parasitol* 91(1): 49-60.

Kang, Y., P. A. Calvo, et al. (1998). "Comparison of humoral immune responses elicited by DNA and protein vaccines based on merozoite surface protein-1 from *Plasmodium yoelii*, a rodent malaria parasite." *J Immunol* 161(8): 4211-9.

Kinnamon, K. E. and W. E. Rothe (1975). "Biological screening in the U.S. Army antimalarial drug development program." *Am J Trop Med Hyg* 24(2): 174-8.

Kwiatkowski, D. and K. Marsh (1997). "Development of a malaria vaccine." *Lancet* 350(9092): 1696-701.

Landgraf, B., H. Kollaritsch, et al. (1994). "*Plasmodium falciparum*: susceptibility in vitro and in vivo to chloroquine and sulfadoxine-pyrimethamine in Ghanaian schoolchildren." *Trans R Soc Trop Med Hyg* 88(4): 440-2.

Londono, J. A., H. Gras-Masse, et al. (1990). "Secondary structure and immunogenicity of hybrid synthetic peptides derived from two *Plasmodium falciparum* pre-erythrocytic antigens." *J Immunol* 145(5): 1557-63.

Marchand, C. and P. Druilhe (1990). "How to select *Plasmodium falciparum* pre-erythrocytic antigens in an expression library without defined probe." Bull World Health Organ 68 *Suppl:* 158-64.

Meis, J. F., T. Ponnudurai, et al. (1990). "*Plasmodium falciparum*: studies on mature exoerythrocytic forms in the liver of the chimpanzee, Pan troglodytes." *Exp Parasitol* 70(1): 1-11.

Mellouk, S., N. Berbiguier, et al. (1990). "Evaluation of an in vitro assay aimed at measuring protective antibodies against sporozoites." *Bull World Health Organ* 68 Suppl: 52-9.

Mellouk, S., R. K. Maheshwari, et al. (1987). "Inhibitory activity of interferons and interleukin 1 on the development of *Plasmodium falciparum* in human hepatocyte cultures." *J Immunol* 139(12): 4192-5.

Perlaza, B. L., M. Arevalo-Herrera, et al. (1998). "Immunogenicity of four *Plasmodium falciparum* preerythrocytic antigens in Aotus lemurinus monkeys." *Infect Immun* 66(7): 3423-8.

Perlaza, B. L., J. P. Sauzet, et al. (2001). "Long synthetic peptides encompassing the *Plasmodium falciparum* LSA3 are the target of human B and T cells and are potent inducers of B helper, T helper and cytolytic T cell responses in mice." *Eur J Immunol* 31(7): 2200-9.

Perlaza, B. L., C. Zapata, et al. (2003). "Immunogenicity and protective efficacy of *Plasmodium falciparum* liver-stage Ag-3 in Aotus lemurinus griseimembra monkeys." *Eur J Immunol* 33(5): 1321-1327.

Ponnudurai, T., A. H. Lensen, et al. (1989). "Infectivity of cultured *Plasmodium falciparum* gametocytes to mosquitoes." *Parasitology* 98 Pt 2: 165-73.

Sauzet, J. P., B. L. Perlaza, et al. (2001). "DNA immunization by *Plasmodium falciparum* liver-stage antigen 3 induces protection against *Plasmodium yoelii* sporozoite challenge." *Infect Immun* 69(2): 1202-6.

Schneider, J., S. C. Gilbert, et al. (1998). "Enhanced immunogenicity for CD8+ T cell induction and complete protective efficacy of malaria DNA vaccination by boosting with modified vaccinia virus Ankara." *Nat Med* 4(4): 397-402.

Schofield, L., A. Ferreira, et al. (1987). "Interferon-gamma inhibits the intrahepatocytic development of malaria parasites in vitro." *J Immunol* 139(6): 2020-5.

Stoute, J. A., M. Slaoui, et al. (1997). "A preliminary evaluation of a recombinant circumsporozoite protein vaccine against *Plasmodium falciparum* malaria. RTS,S Malaria Vaccine Evaluation Group." *N Engl J Med* 336(2): 86-91.

Theisen, M. et al 2000, Vaccine September 15; 19(2-3):204-12

Trape, J. F., C. Rogier, et al. (1994). "The Dielmo project: a longitudinal study of natural malaria infection and the mechanisms of protective immunity in a community living in a holoendemic area of Senegal." *Am J Trop Med Hyg* 51(2): 123-37.

Valenzuela, J. G., Y. Belkaid, et al. (2001). "Toward a defined anti-Leishmania vaccine targeting vector antigens: characterization of a protective salivary protein." *J Exp Med* 194 (3): 331-42.

Zapata, J. C., B. L. Perlaza, et al. (2002). "Reproducible infection of intact Aotus lemurinus griseimembra monkeys by *Plasmodium falciparum* sporozoite inoculation." *J Parasitol* 88(4): 723-9.

---

The invention claimed is:

1. An isolated antigenic polypeptide, comprising at least a consensus LSA-5 peptide of sequence EEVVEELIEEVIPEELVL (SEQ ID NO: 15).

2. An isolated antigenic polypeptide, which comprises the LSA-5 antigen of SEQ ID NO: 24-16, wherein the polypeptide induces protection in a subject against *Plasmodium falciparum* sporozoites following immunization of the subject with the polypeptide.

3. An antigenic polypeptide consisting of a fusion protein comprising an antigenic moiety which is a polypeptide according to claim 1 or claim 2, and a second moiety which is heterologous to the LSA-5 antigen.

4. An antigenic lipo-polypeptide, which is a polypeptide according to claim 1, wherein a lipidic molecule is linked to the polypeptide.

5. The lipo-polypeptide of claim 4, wherein the lipidic molecule is a C-terminal palmitoylysylamide residue.

6. An immunogenic composition comprising as an immunogen, the polypeptide according to claim 2.

7. A vaccine against malaria comprising as an immunogen the polypeptide according to claim 2.

8. The immunogenic composition of claim 6 or the vaccine of claim 7, further comprising at least one antigen selected from the group consisting of LSA-1, LSA-3, LSA 5, SALSA, STARP, TRAP, PfEXP1, CS, MSP-3, P126-CERP-SERA and GLURP.

9. The immunogenic composition according to claim 6 or vaccine according to claim 7, which is formulated to elicit IgG1 or IgG3 classes of antibodies that are cytophilic.

10. The immunogenic composition or the vaccine according to claim 6 or the vaccine according to claim 7, which is formulated for intradermal or intramuscular injection.

11. The immunogenic composition or vaccine of claim 10, comprising between 1 and 100 µg of immunogen per injection dose, preferably between 2 and 50 µg.

12. The immunogenic composition of claim 6, for prevention or treatment of pre-erythrocytic stages of *Plasmodium* infection.

13. The immunogenic composition of claim 6, for prevention or treatment of blood stages of *Plasmodium* infection.

14. The immunogenic composition of claim 6, further comprising SBAS2 and/or Alum and/or Montanide as an adjuvant.

15. A kit for the in vitro diagnosis of malaria, comprising at least the polypeptide according to claim 2.

16. The kit of claim 15, wherein the antigenic polypeptide is bound to a support.

17. The kit of claim 15 or 16, further comprising reagents for enabling the formation of antigen/antibody complexes between said antigenic peptide or polypeptide and the antibodies possibly present in a biological sample, and reagents enabling the in vitro detection of the antigen/antibody complexes possibly formed.

18. The isolated antigenic polypeptide of claim 2, wherein the isolated antigenic polypeptide consists of the LSA-5 antigen of SEQ ID NO: 16.

19. The isolated polypeptide of claim 2, wherein the isolated antigenic polypeptide comprises no more than 150 amino acids.

20. An antigenic lipo-polypeptide, which is a polypeptide according to claim 2, wherein a lipidic molecule is linked to the polypeptide.

21. An immunogenic composition comprising as an immunogen, the lipopolypeptide according to claim 4.

22. A vaccine against malaria comprising as an immunogen, the lipo-polypeptide according to claim 4.

23. The immunogenic composition of claim 21 or the vaccine of claim 22, further comprising at least one antigen selected from the group consisting of LSA-1, LSA-3, SALSA, STARP, TRAP, PfEXP1, CS, MSP-3, P126-CERP-SERA and GLURP.

24. The immunogenic composition according to claim 21 or vaccine according to claim 22, which is formulated to elicit IgG1 or IgG3 classes of antibodies that are cytophilic.

25. The immunogenic composition or the vaccine according to claim 21 or the vaccine according to claim 22, which is formulated for intradermal or intramuscular injection.

26. The immunogenic composition or vaccine of claim 25, comprising between 1 and 100 µg of immunogen per injection dose, preferably between 2 and 50 µg.

27. The immunogenic composition of claim 21, for prevention or treatment of pre-erythrocytic stages of *Plasmodium* infection.

28. The immunogenic composition of claim 21, for prevention or treatment of blood stages of *Plasmodium* infection.

29. The immunogenic composition of claim 21, further comprising SBAS2 and/or Alum and/or Montanide as an adjuvant.

* * * * *

SEQUENCE LISTING

```
<160> NUMBER OF SEQ ID NOS: 24

<210> SEQ ID NO 1
<211> LENGTH: 9
<212> TYPE: PRT
<213> ORGANISM: Plasmodium falciparum

<400> SEQUENCE: 1

Glu Glu Gln Ile Glu Glu Val Ile Gln
1               5

<210> SEQ ID NO 2
<211> LENGTH: 9
<212> TYPE: PRT
<213> ORGANISM: Plasmodium falciparum

<400> SEQUENCE: 2

Glu Glu Ile Ile Glu Gln Val Val Pro
1               5

<210> SEQ ID NO 3
<211> LENGTH: 9
<212> TYPE: PRT
<213> ORGANISM: Plasmodium falciparum

<400> SEQUENCE: 3

Glu Glu Leu Ile Glu Glu Val Val Pro
1               5
```

```
<210> SEQ ID NO 4
<211> LENGTH: 9
<212> TYPE: PRT
<213> ORGANISM: Plasmodium falciparum

<400> SEQUENCE: 4

Glu Glu Ile Ile Glu Glu Val Ile Pro
1               5

<210> SEQ ID NO 5
<211> LENGTH: 9
<212> TYPE: PRT
<213> ORGANISM: Plasmodium falciparum

<400> SEQUENCE: 5

Glu Glu Ile Val Glu Glu Val Ile Tyr
1               5

<210> SEQ ID NO 6
<211> LENGTH: 5
<212> TYPE: PRT
<213> ORGANISM: Plasmodium falciparum

<400> SEQUENCE: 6

Glu Glu Val Ile Pro
1               5

<210> SEQ ID NO 7
<211> LENGTH: 9
<212> TYPE: PRT
<213> ORGANISM: Plasmodium falciparum

<400> SEQUENCE: 7

Glu Glu Leu Val Glu Glu Val Ile Ala
1               5

<210> SEQ ID NO 8
<211> LENGTH: 9
<212> TYPE: PRT
<213> ORGANISM: Plasmodium falciparum

<400> SEQUENCE: 8

Glu Lys Leu Val Lys Glu Ile Val Pro
1               5

<210> SEQ ID NO 9
<211> LENGTH: 9
<212> TYPE: PRT
<213> ORGANISM: Plasmodium falciparum

<400> SEQUENCE: 9

Glu Gln Val Arg Glu Glu Val Ile Leu
1               5

<210> SEQ ID NO 10
<211> LENGTH: 9
<212> TYPE: PRT
<213> ORGANISM: Plasmodium falciparum

<400> SEQUENCE: 10

Glu Glu Ile Val Glu Glu Met Ile Pro
1               5
```

```
<210> SEQ ID NO 11
<211> LENGTH: 9
<212> TYPE: PRT
<213> ORGANISM: Plasmodium falciparum

<400> SEQUENCE: 11

Glu Glu Phe Val Glu Glu Val Ala Pro
1               5

<210> SEQ ID NO 12
<211> LENGTH: 9
<212> TYPE: PRT
<213> ORGANISM: Plasmodium falciparum

<400> SEQUENCE: 12

Glu Val Glu Ile Glu Glu Ile Ile Pro
1               5

<210> SEQ ID NO 13
<211> LENGTH: 9
<212> TYPE: PRT
<213> ORGANISM: Plasmodium falciparum

<400> SEQUENCE: 13

Glu Glu Leu Ile Glu Glu Val Ile Pro
1               5

<210> SEQ ID NO 14
<211> LENGTH: 9
<212> TYPE: PRT
<213> ORGANISM: Plasmodium falciparum

<400> SEQUENCE: 14

Glu Glu Leu Ile Glu Lys Val Ile Pro
1               5

<210> SEQ ID NO 15
<211> LENGTH: 18
<212> TYPE: PRT
<213> ORGANISM: Plasmodium falciparum

<400> SEQUENCE: 15

Glu Glu Val Val Glu Glu Leu Ile Glu Glu Val Ile Pro Glu Glu Leu
1               5                   10                  15

Val Leu

<210> SEQ ID NO 16
<211> LENGTH: 133
<212> TYPE: PRT
<213> ORGANISM: Plasmodium falciparum

<400> SEQUENCE: 16

Ile Pro Glu Glu Gln Ile Glu Glu Val Ile Gln Glu Ile Ile Glu
1               5                   10                  15

Gln Val Val Pro Glu Glu Leu Ile Glu Glu Val Val Pro Glu Glu Ile
            20                  25                  30

Ile Glu Glu Val Ile Pro Glu Glu Ile Val Glu Glu Val Ile Tyr Glu
        35                  40                  45

Glu Val Ile Pro Glu Glu Leu Val Glu Glu Val Ile Ala Glu Lys Leu
    50                  55                  60

Val Lys Glu Ile Val Pro Glu Gln Val Arg Glu Glu Val Ile Leu Glu
65                  70                  75                  80
```

```
Glu Ile Val Glu Glu Met Ile Pro Glu Glu Phe Val Glu Glu Val Ala
                85                  90                  95

Pro Glu Val Glu Ile Glu Glu Ile Ile Pro Glu Glu Leu Ile Glu Glu
            100                 105                 110

Val Ile Pro Glu Val Leu Val Glu Glu Ala Val Pro Glu Glu Leu Ile
        115                 120                 125

Glu Lys Val Ile Pro
    130

<210> SEQ ID NO 17
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Glu, Lys or not present
<220> FEATURE:
<221> NAME/KEY: MOD_RES
<222> LOCATION: (3)..(4)
<223> OTHER INFORMATION: Val or Ile
<220> FEATURE:
<221> NAME/KEY: MOD_RES
<222> LOCATION: (9)..(9)
<223> OTHER INFORMATION: Ile, Val or Arg
<220> FEATURE:
<221> NAME/KEY: MOD_RES
<222> LOCATION: (11)..(11)
<223> OTHER INFORMATION: Glu or Lys
<220> FEATURE:
<221> NAME/KEY: MOD_RES
<222> LOCATION: (14)..(14)
<223> OTHER INFORMATION: Pro or Ala
<220> FEATURE:
<221> NAME/KEY: MOD_RES
<222> LOCATION: (16)..(16)
<223> OTHER INFORMATION: Glu, Val or Lys
<220> FEATURE:
<221> NAME/KEY: MOD_RES
<222> LOCATION: (17)..(17)
<223> OTHER INFORMATION: Leu or Ile
<220> FEATURE:
<221> NAME/KEY: MOD_RES
<222> LOCATION: (18)..(18)
<223> OTHER INFORMATION: Val or Ile

<400> SEQUENCE: 17

Xaa Glu Xaa Xaa Pro Glu Glu Leu Xaa Glu Xaa Val Ile Xaa Glu Xaa
1               5                   10                  15

Xaa Xaa

<210> SEQ ID NO 18
<211> LENGTH: 398
<212> TYPE: DNA
<213> ORGANISM: Plasmodium falciparum

<400> SEQUENCE: 18
attccagaag aacaaattga agaggttata caagaagaaa taattgaaca agttgtacca      60
gaagaattaa ttgaagaagt tgtaccagaa gaaataattg aagaggttat accagaagaa     120
atagttgaag aggtaatata tgaagaggtg atacctgaag aactagtaga agaagttata     180
gctgagaaac tggttaaaga gattgtacca gaacaagttc gtgaagaagt aacattagag     240
gaaatcgttg aggagatgat acccgaagaa tttgtagaag aggttgcacc agaagttgaa     300
```

```
atcgaggaaa taattcctga ggaattaata gaagaagtta taccagaggt attagttgaa      360
gaggctgtac cagaagaact aatagaaaaa gttatacc                              398
```

<210> SEQ ID NO 19
<211> LENGTH: 132
<212> TYPE: PRT
<213> ORGANISM: Plasmodium falciparum

<400> SEQUENCE: 19

Ile Pro Glu Glu Gln Ile Glu Glu Val Ile Gln Glu Ile Ile Glu
1               5                   10                  15

Gln Val Val Pro Glu Glu Leu Ile Glu Glu Val Val Pro Glu Glu Ile
            20                  25                  30

Ile Glu Glu Val Ile Pro Glu Glu Ile Val Glu Glu Val Ile Tyr Glu
        35                  40                  45

Glu Val Ile Pro Glu Glu Leu Val Glu Glu Val Ile Ala Glu Lys Leu
    50                  55                  60

Val Lys Glu Ile Val Pro Glu Gln Val Arg Glu Glu Val Thr Leu Glu
65                  70                  75                  80

Glu Ile Val Glu Glu Met Ile Pro Glu Glu Phe Val Glu Glu Val Ala
                85                  90                  95

Pro Glu Val Glu Ile Glu Glu Ile Ile Pro Glu Glu Leu Ile Glu Glu
            100                 105                 110

Val Ile Pro Glu Val Leu Val Glu Glu Ala Val Pro Glu Glu Leu Ile
        115                 120                 125

Glu Lys Val Ile
    130

<210> SEQ ID NO 20
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (19)..(19)
<223> OTHER INFORMATION: Palmitoylysylamide residue

<400> SEQUENCE: 20

Glu Glu Val Val Glu Glu Leu Ile Glu Glu Val Ile Pro Glu Glu Leu
1               5                   10                  15

Val Leu Xaa

<210> SEQ ID NO 21
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Tyr Pro Glu Glu Leu Val Glu Glu Val Ile Pro Glu Glu Leu Val Glu
1               5                   10                  15

Glu Val Ile Pro Lys
            20

```
<210> SEQ ID NO 22
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Glu or Lys
<220> FEATURE:
<221> NAME/KEY: MOD_RES
<222> LOCATION: (3)..(4)
<223> OTHER INFORMATION: Val or Ile
<220> FEATURE:
<221> NAME/KEY: MOD_RES
<222> LOCATION: (9)..(9)
<223> OTHER INFORMATION: Ile, Val or Arg
<220> FEATURE:
<221> NAME/KEY: MOD_RES
<222> LOCATION: (11)..(11)
<223> OTHER INFORMATION: Glu or Lys
<220> FEATURE:
<221> NAME/KEY: MOD_RES
<222> LOCATION: (14)..(14)
<223> OTHER INFORMATION: Pro or Ala
<220> FEATURE:
<221> NAME/KEY: MOD_RES
<222> LOCATION: (16)..(16)
<223> OTHER INFORMATION: Glu, Val or Lys
<220> FEATURE:
<221> NAME/KEY: MOD_RES
<222> LOCATION: (17)..(17)
<223> OTHER INFORMATION: Leu or Ile
<220> FEATURE:
<221> NAME/KEY: MOD_RES
<222> LOCATION: (18)..(18)
<223> OTHER INFORMATION: Val or Ile
<220> FEATURE:
<221> NAME/KEY: MOD_RES
<222> LOCATION: (20)..(20)
<223> OTHER INFORMATION: Palmitoylysylamide residue

<400> SEQUENCE: 22

Xaa Glu Xaa Xaa Pro Glu Glu Leu Xaa Glu Xaa Val Ile Xaa Glu Xaa
1               5                   10                  15

Xaa Xaa Lys Xaa
            20

<210> SEQ ID NO 23
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 23

His His His His His His
1               5

<210> SEQ ID NO 24
<211> LENGTH: 9
<212> TYPE: PRT
<213> ORGANISM: Plasmodium falciparum

<400> SEQUENCE: 24

Glu Val Leu Val Glu Glu Ala Val Pro
1               5
```